(12) United States Patent
Park et al.

(10) Patent No.: US 8,968,716 B2
(45) Date of Patent: Mar. 3, 2015

(54) IN SITU-FORMING HYDROGEL FOR TISSUE ADHESIVES AND BIOMEDICAL USE THEREOF

(75) Inventors: Ki-Dong Park, Seoul (KR); Yoon-Ki Joung, Incheon (KR); Kyung-Min Park, Anyang-si (KR); Eu-Gene Lih, Seoul (KR)

(73) Assignee: Ajou University Industry-Academic Cooperation Foundation, Gyeonggi-Do (KR)

( * ) Notice: Subject to any disclaimer, the term of this patent is extended or adjusted under 35 U.S.C. 154(b) by 0 days.

(21) Appl. No.: 13/393,094

(22) PCT Filed: Sep. 2, 2010

(86) PCT No.: PCT/KR2010/005953
§ 371 (c)(1),
(2), (4) Date: Feb. 28, 2012

(87) PCT Pub. No.: WO2011/028031
PCT Pub. Date: Mar. 10, 2011

(65) Prior Publication Data
US 2012/0156164 A1 Jun. 21, 2012

(30) Foreign Application Priority Data
Sep. 4, 2009 (KR) .......................... 10-2009-0083639

(51) Int. Cl.
| | | |
|---|---|---|
| A61L 24/04 | (2006.01) | |
| A61L 24/08 | (2006.01) | |
| A61K 38/39 | (2006.01) | |
| A61K 31/722 | (2006.01) | |
| A61K 31/765 | (2006.01) | |
| A61K 38/02 | (2006.01) | |
| A61K 38/18 | (2006.01) | |
| A61K 38/27 | (2006.01) | |
| A61K 38/19 | (2006.01) | |
| A61K 38/20 | (2006.01) | |
| A61K 38/23 | (2006.01) | |
| A61K 38/25 | (2006.01) | |
| A61K 38/28 | (2006.01) | |
| A61K 38/31 | (2006.01) | |
| A61K 38/26 | (2006.01) | |
| A61K 39/395 | (2006.01) | |
| A61K 39/00 | (2006.01) | |
| A61K 33/24 | (2006.01) | |
| A61L 24/00 | (2006.01) | |

(Continued)

(52) U.S. Cl.
CPC ......... *A61L 24/0042* (2013.01); *A61L 24/0015* (2013.01); *A61L 24/0031* (2013.01); *A61L 24/046* (2013.01); *A61L 27/18* (2013.01); *A61L 27/52* (2013.01); *A61L 27/54* (2013.01); *A61L 27/58* (2013.01); *A61L 2300/252* (2013.01); *A61L 2300/256* (2013.01); *A61L 2300/406* (2013.01); *A61L 2300/41* (2013.01); *A61L 2300/414* (2013.01); *A61L 2300/416* (2013.01); *A61L 2300/426* (2013.01); *A61L 2300/43* (2013.01); *A61L 2300/602* (2013.01)
USPC ....... 424/78.3; 424/85.2; 424/85.5; 424/85.6; 424/85.7; 424/141.1; 424/184.1; 424/649; 424/85.1; 514/11.9; 514/8.4; 514/11.2; 514/9.7; 514/6.5; 514/11.1; 514/11.7; 514/17.2; 514/1.1; 514/9.1; 514/8.1; 514/8.9; 514/8.8; 514/11.4; 514/11.3; 514/7.7; 514/9.6; 514/8.2

(58) Field of Classification Search
CPC ............ A61L 24/0015; A61L 24/0031; A61L 24/0042; A61L 24/046; A61L 2300/602; A61L 2300/43; A61L 2300/414; A61L 2300/416
USPC ......... 424/78.3, 85.2, 85.5, 85.6, 85.7, 141.1, 424/184.1, 64, 649, 78, 85.1; 514/11.9, 8.4, 514/11.2, 9.7, 6.5, 11.1, 11.7, 118, 17.2, 55, 514/1.1, 9.1, 8.1, 8.9, 8.8, 11.4, 11.3, 7.7, 514/9.6, 8.2
See application file for complete search history.

(56) References Cited

U.S. PATENT DOCUMENTS

| 7,208,171 B2 | 4/2007 | Messersmith et al. |
|---|---|---|
| 2003/0087338 A1 | 5/2003 | Messersmith et al. |

(Continued)

FOREIGN PATENT DOCUMENTS

| KR | 10-2007-0038738 A | 4/2007 |
|---|---|---|
| KR | 10-2009-0002946 A | 1/2009 |

(Continued)

OTHER PUBLICATIONS

Park et al (Biomolecules Feb. 1, 2010, p. 706).*

(Continued)

*Primary Examiner* — Suzanne Ziska
*Assistant Examiner* — Thurman Wheeler
(74) *Attorney, Agent, or Firm* — Revolution IP, PLLC

(57) ABSTRACT

Disclosed herein are an in situ-forming, bioadhesive hydrogel and the medical uses thereof. Being formed by in situ crosslinking through an enzymatic reaction, the hydrogel has an advantage over conventional bioadhesive hydrogels in terms of biocompatibility. In addition, the in situ-forming bioadhesive hydrogel has excellent biocompatibility and mechanical strength and has excellent tissue adhesiveness thanks to modification with/without dopa derivatives. The hydrogel finds a variety of applications in the biomedical field, including bioadhesives or hemostats, implant substances for tissue regeneration and augmentation, carriers for delivering biologically active materials or drugs, etc.

11 Claims, 11 Drawing Sheets

(51) Int. Cl.
*A61L 27/18* (2006.01)
*A61L 27/52* (2006.01)
*A61L 27/54* (2006.01)
*A61L 27/58* (2006.01)

(56) References Cited

U.S. PATENT DOCUMENTS

2007/0208141 A1 9/2007 Shull et al.
2008/0149566 A1 6/2008 Messersmith et al.
2008/0247984 A1 10/2008 Messersmith et al.
2009/0163661 A1 6/2009 Shull et al.

FOREIGN PATENT DOCUMENTS

| WO | WO 00/09199 A1 | 2/2000 |
|---|---|---|
| WO | WO 2008/049108 A1 | 4/2008 |
| WO | WO 2008/091386 A2 | 7/2008 |

OTHER PUBLICATIONS

Kaul et al (pharmaceutical Research, vol. 19, No. 7, Jul. 2002).*
Sakai et al (Biomaterials, 30, Apr. 5, 2009).*
Kushibiki et al (Biomaterials, 2004, p. 202).*
Motoichi Kurisawa et al., "Injectable biodegradable hydrogels composed of hyaluronic . . . ", Chem. Commun., 2005 pp. 4312-4314, The Royal Society of Chemistry.
Hyung Joon Cha et al., "Development of bioadhesive from marine mussels", Journal of Adhesion and Interface, 2008, pp. 34-42, vol. 9, No. 4.

* cited by examiner

Tet-TA/DA hydrogel

Tet-TA/DA II/CHPA or Tet-TA/DA II/GHPA

Tet-TA/DA II/GPEG-TA or Tet-TA/DA II/CPEG-TA hydrogels

*Tet-TADA: Tetronic-tyramine/dopamine
GPEG-TA: Gelatin-PEG-TA
CPEG-TA: Chitosan-PEG-TA Fig. 17
Fig. 18
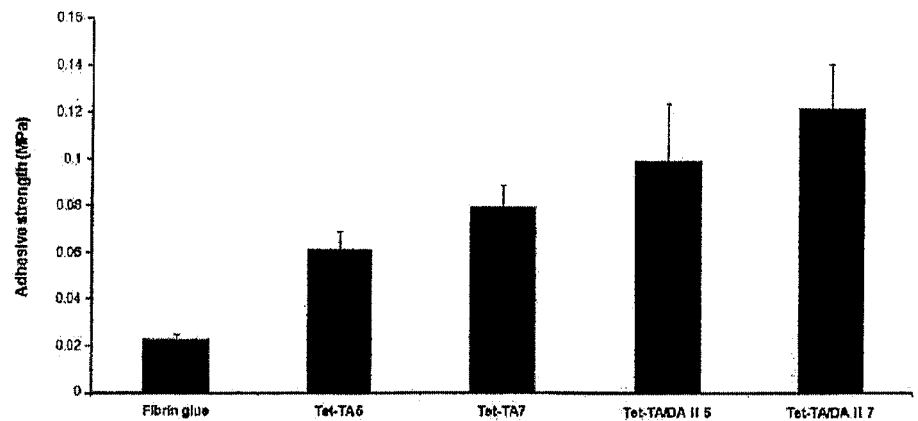
Fig. 19
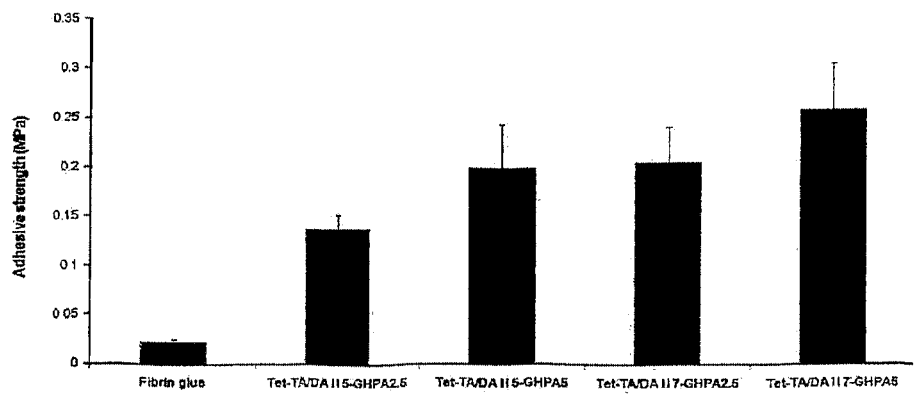

IN SITU-FORMING HYDROGEL FOR TISSUE ADHESIVES AND BIOMEDICAL USE THEREOF

CROSS REFERENCE TO PRIOR APPLICATIONS

This application is a National Stage Patent Application of PCT International Patent Application No. PCT/KR2010/005953 (filed on Sep. 2, 2010) under 35 U.S.C. §371, which claims priority to Korean Patent Application No. 10-2009-0083639 (filed on Sep. 4, 2009), which are all hereby incorporated by reference in their entirety.

TECHNICAL FIELD

The present invention relates to in situ-forming bioadhesive hydrogel which is excellent in biocompatibility and mechanical strength and shows excellent bioadhesiveness, with a dopa derivative bonded thereto, and the biomedical uses thereof.

BACKGROUND ART

The market for wound care, the major proportion of which is for sealants and hemostats, has grown rapidly alongside great advances in the research and development of tissue adhesives. Triggered by the FDA granting permission to a fibrin sealant in 1998, a burst of novel tissue adhesives has been appearing in the market each year. Attention is now being focused on these tissue adhesives as alternatives to those used in conventional surgical or internal operations, such as suturing, clipping, cautery, etc.

Conventional surgical techniques, such as suturing, guarantee strong tensile strength, but have the disadvantages of pain and the need for the threads to be postoperatively removed. On the other hand, tissue adhesives enjoy the advantages of a short adhesion time, simple usage, no requirements for postoperative removal, etc., but are problematic in that they exhibit low adhesiveness, poor biocompatibility and tensile strength and a remarkably decreased adhesiveness particularly in the presence of moisture. Studies have focused on conquering the problems.

The necessity for direct contact with the tissue forces tissue adhesives to have biocompatibility. Further, because they are typically used inside the body, for example, in places where they may be brought into direct contact with body fluids or blood, more stringent conditions regarding toxicity and harmfulness must be applied to medical adhesives, as well as strict standards for biocompatibility and biodegradation.

Although they must show properties corresponding to the different regions or fields to which they are applied, such as skins, vessels, digestive organs, cranial nerves, plastic surgery, orthopedic surgery, general surgery etc., tissue adhesives are required to have in common the following properties: 1) must adhere fast to target regions at room temperature under atmospheric pressure even in the presence of moisture; 2) must be free of toxicity and be capable of being sterilized; 3) must maintain sufficient mechanical strength and be in close contact with a wound surface; 4) must be biodegradable and capable of controlling hemostasis; and 5) must be effective for wound healing.

Among currently commercialized and/or utilized tissue adhesives are instant cyanoacrylate glues, fibrin glues, gelatin glues, and polyurethane. Attention has recently been paid to instant cyanoacrylate glues because of their high adhesiveness and performance. Particularly, instant glues for tissue closure, having biocompatibility, flexibility and low toxicity, have been under extensive study in advanced countries thanks to their beneficial effects including hemostasis, antibacterial activity and being able to substitute for sutures.

Cyanoacrylate tissue adhesives are commercially available under the trade names of Dermabond (Johnson & Johnson) or Indermil (US Surgical). These cyanoacrylate adhesives, consisting of a solitary material, can solidify in a short period of time at room temperature just by using water without the aid of initiators and exhibit a transparent appearance and strong adhesive strength, but low resistance to both impact and heat. Moreover, their use is now restricted due to the high toxicity and fragility thereof although cyanoacrylate adhesives are partially used in the clinical field. Fibrin glues received FDA approval first in 1998 and since then they have been applied to cardiac surgery. Active research into fibrin sealants has lead to the commercialization of products, e.g., Tisseel VH® (Baxer) and Evicel™ (Johnson & Johnson).

Together with cyanoacrylate sealants, fibrin sealants occupy a predominant share of the tissue adhesive market. Taking advantage of the clotting of fibrin, the two major ingredients of fibrin sealants are fibrinogen and thrombin in combination with calcium chloride and factor XIII. As alternatives or reinforcements to suturing, they are applied to the closure of peripheral nerves and very small blood vessels.

Fibrin sealants have several advantages over older methods of hemostasis; they speed up the formation of a stable clot independently of water in target sites, and additionally, they can form a clot in conjunction with platelets without restrictions and are excellent in biocompatibility. However, they suffer from the disadvantages of weak adhesive strength, fast biodegradation and infection risk.

Gelatin glues, derived from the body, are a kind of tissue adhesive developed with gelatin-resorcinol-formalin (GRF). In addition, there are tissue adhesives made of gelatin-glutaraldehyde. Although these tissue adhesives provide high adhesiveness, formalin or glutaraldehyde undergo crosslinking reactions with proteins of the target tissues, giving rise to tissue toxicity.

Developed as flexible adhesives, polyurethane adhesives can maintain the closures in their natural state following solidification. These adhesives absorb water from tissue surfaces to stick themselves fast to the tissues. They react with water to be cured within several minutes and the cured adhesives biodegrade properly in addition to being flexible. However, aromatic diisocyanate, a material used in polyurethane adhesives, is toxic to the body.

Thus, the tissue adhesives developed so far still have disadvantages in terms of toxicity and weak adhesiveness. As a solution to these problems, 3,4-dihydroxyphenyl-L-alanine (DOPA) is becoming popular and is under intensive study.

Dopa is a naturally occurring amino acid. In the presence of polyphenol oxidase, tyrosine, abundantly found in the foot of mussels, is hydroxylated to dopa. This amino acid forms a very strong hydrogen bond with hydrophilic surfaces and a strong coordinate covalent bond with metals or semi-metals. Being oxidized to dopa-quinone, dopa residues function to crosslink protein molecules.

Dopa-based tissue adhesives are commercially available, identified as Cell-Tak™ (BD Bioscience Clontech) and MAP™ (Swedish BioScience Lab.). However, these products require as many as 10,000 mussels to make 1 gram of the foot protein. Such a low extraction yield and high production cost restrict the use of the adhesive. In practice, the products are used mainly in cell or tissue culturing.

In order to overcome the problems encountered in the prior art, Professor Cha, Postech University, Korea developed a method of extracting mussel foot proteins. A tissue adhesive developed on the basis of the method of Cha was found to have an adhesive strength four-fold higher than that of fibrin glues (Cha et al., Journal of Adhesion and Interfaces 2008). However, this method also, although much improved, does not provide a satisfactory production yield, which remains only at 50-60% in the course of protein purification.

Another tissue adhesive based on dopa was developed by Professor Phillip B. Messersmith in 2007. It was an injectable and bioadhesive polymeric hydrogel which is prepared from a PEG-diamine modified with glutamine substrates with the aid of an enzyme (Phillip B. Messersmith et al., U.S. Pat. No. 7,208,171 B2). The prepared hydrogel, however, retains a mechanical strength of approximately 100 Pa and has an adhesive strength that is as high as or twice as high as that of fibrin glue. Phillip B. Messersmith also developed an in situ gel-forming bioadhesive hydrogel based on branched-PEG or PMMA-PtBMA-PMMA triblock, both modified with dopa derivatives, and a surface coating method (Phillip B. Messersmith et al., US2008/0247984 A1, US2007/0208141 A1, US2008/04149566 A1, US2009/0163661 A1, US2003/0087338 A1, WO2008/049108 A1, WO2008/091386 A2).

The dopa derivative-conjugated hydrogel exhibits high adhesive strength, overcoming the previous problems. However, at least 30 sec is required for gelling and a toxic oxidant, such as $NaIO_4$, $FeCl_3$, etc., is used for hydrogel crosslinking.

There is therefore in the context of in situ formation, a great need for bioadhesive hydrogel that requires a short gelation time and exhibits excellent mechanical strength, good biocompatibility, proper biodegradation, and fast and strong adhesiveness even in the presence of water.

DISCLOSURE OF INVENTION

Technical Problem

Leading to the present invention, intensive and thorough research into bioadhesives, conducted by the present inventors, aiming to overcome the problems encountered in the prior art, resulted in the finding that a hydrogel shows excellent biocompatibility and mechanical strength when a synthetic polymer is hybridized with a naturally occurring polymer and has excellent bioadhesiveness when it is modified with a dopa derivative.

It is therefore an object of the present invention to provide an in situ-forming, bioadhesive hydrogel which has excellent bioadhesiveness in addition to showing excellent biostability, biocompatibility and mechanical strength.

It is another object of the present invention to provide the use of the in situ-forming hydrogel excellent in biostability, biocompatibility, mechanical strength and bioadhesiveness as a material for bioadhesives and hemostats.

It is a further object of the present invention to provide the use of the in situ-forming hydrogel excellent in biostability, biocompatibility, mechanical strength and bioadhesiveness as an implant material for tissue regeneration and augmentation.

It is still a further object of the present invention to provide the use of the in situ-forming hydrogel excellent in biostability, biocompatibility, mechanical strength and bioadhesiveness as a carrier for delivering biologically active materials or drugs.

Technical Solution

The present invention provides in situ-forming, bioadhesive hydrogel, represented by one of the following Chemical Formulas 4 to 7, in which two or more homogeneous or heterogeneous polymers selected from a group consisting of: i) a star-shaped polymer, represented by the following Chemical Formula 1, in which one or more compounds selected from among phenol, aniline and derivatives thereof are modified with one or more compounds selected from among dopa and derivatives thereof; ii) a heterogeneous blend, comprising the star-shaped polymer of Chemical Formula 1 and a branched polymer, represented by the following Chemical Formula 2, in which a polymer backbone is grafted with one or more compounds selected from among phenol, aniline and, derivatives thereof, with or without a water-soluble polymer serving as a linker therebetween; and iii) a branched polymer, represented by the following Chemical Formula 3, in which a polymer backbone is grafted with one or more compounds selected from among phenol, aniline and derivatives thereof, with or without a water-soluble polymer serving as a linker therebetween, are bonded to each other through dehydrogenation between the phenol, aniline, dopa and derivatives thereof on adjacent polymers.

Advantageous Effects

The present invention provides an in situ-forming bioadhesive hydrogel which has excellent biocompatibility and mechanical strength and excellent tissue adhesiveness thanks to modification with/without dopa derivatives. Particularly, the hydrogel according to the present invention finds a variety of applications in the biomedical field, including: bioadhesives or hemostats; in situ-forming, tissue engineering scaffold; sustained release drug delivery systems for proteins, DNA, growth factors, cells, etc.; tissue augmentation; wound healing; and prevention of organ adhesion.

BRIEF DESCRIPTION OF DRAWINGS

The above and other objects, features and advantages of the present invention will be more clearly understood from the following detailed description taken in conjunction with the accompanying drawings, in which:

FIG. 17 is a set of photographs showing the biocompatibility of Tet-TA/DA II, Tet-TA/DA II+GPEG-TA, Tet-TA/DA II+CPEG-TA, HA-PEG-TA/TA, CMC-PEG-TA/DA, and AGL-PEG-TA/DA hydrogel to 2D cells, FIGS. 18 to 24 are graphs showing adhesive strengths of the hydrogels Tet-TA and Tet-TA/DA II (A), Tet-TA/DAII+GHPA (B), Tet-TA/DAII+CHPA (C), Tet-TA/DAII+GPEG-TA (D), Tet-TA/DAII+CPEG-TA (E), GPEG-TA, CPEG-TA, Tet-TA+GPEG-TA, Tet-TA+CPEG-TA (F), and HA-PEG-TA/DA, CMC-PEG-TA/DA, ALG-PEG-TA/DA (G), with fibrin glue and cyamoacrylate serving as controls.

BEST MODE FOR CARRYING OUT THE INVENTION

In accordance with one aspect thereof, the present invention provides in situ-forming, bioadhesive hydrogel, represented by one of the following Chemical Formulas 4 to 7, in which two or more homogeneous or heterogeneous polymers selected from a group consisting of: i) a star-shaped polymer, represented by the following Chemical Formula 1, in which one or more compounds selected from among phenol, aniline and derivatives thereof are modified with one or more compounds selected from among dopa and derivatives thereof; ii) a heterogeneous blend, comprising the star-shaped polymer of Chemical Formula 1 and a branched polymer, represented by the following Chemical Formula 2, in which a polymer backbone is grafted with one or more compounds selected from among phenol, aniline and, derivatives thereof, with or without a water-soluble polymer serving as a linker therebetween; and iii) a branched polymer, represented by the following Chemical Formula 3, in which a polymer backbone is grafted with one or more compounds selected from among phenol, aniline and derivatives thereof, with or without a water-soluble polymer serving as a linker therebetween, are bonded to each other through dehydrogenation between the phenol, aniline, dopa and derivatives thereof on adjacent polymers.

Figure 1:
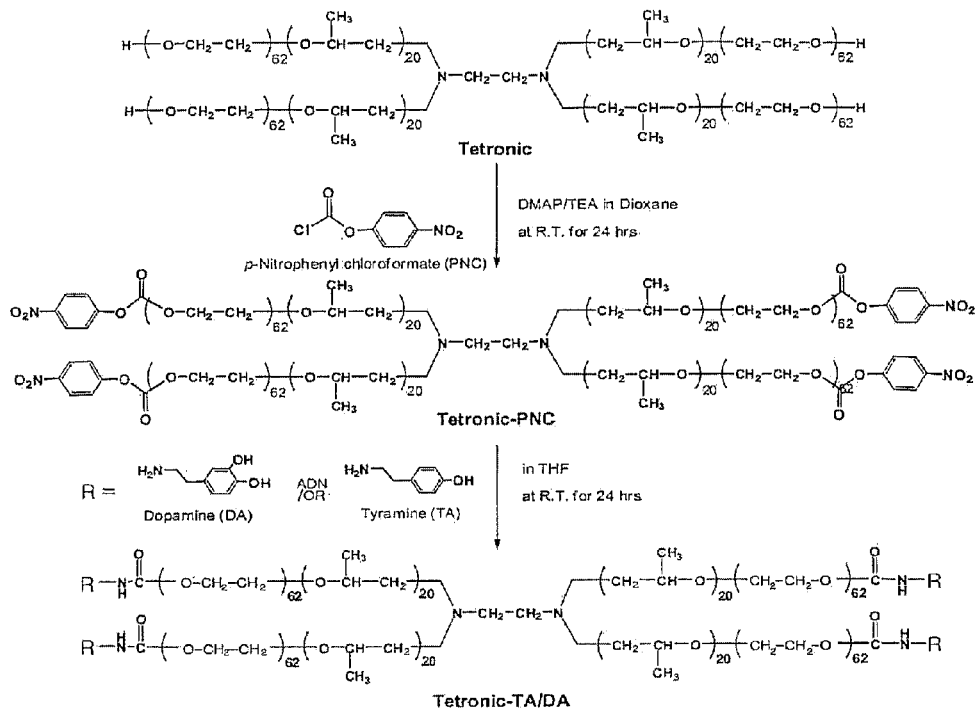
FIG. 1 is a reaction scheme showing the synthesis of Tet-TA/DA.

Chemistry FIG. 1

[Chem. 1]

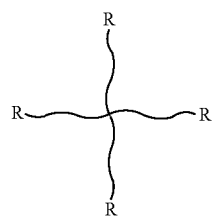

Figure 2:
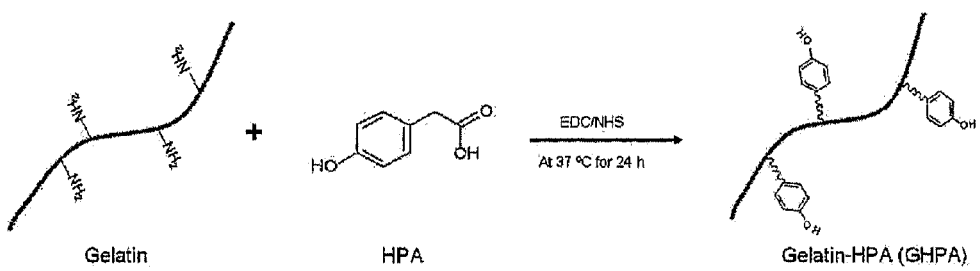
FIG. 2 is a reaction scheme showing the synthesis of GHPA.

Chemistry FIG. 2

[Chem. 2]

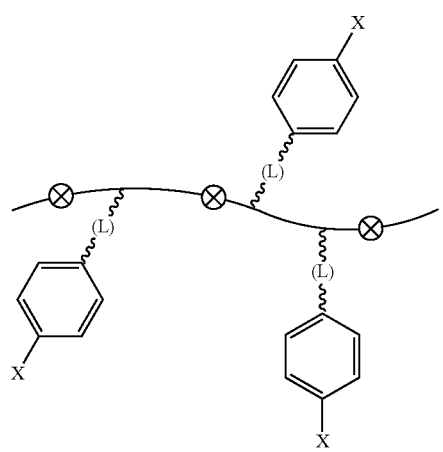

Figure 3:
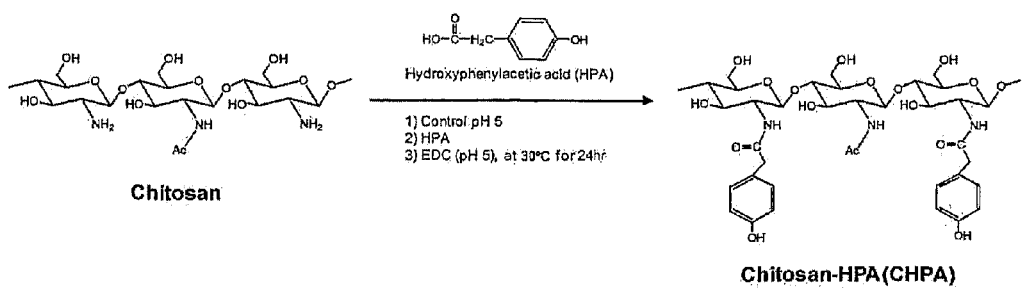
FIG. 3 is a reaction scheme showing the synthesis of CHPA.
Figure 4:
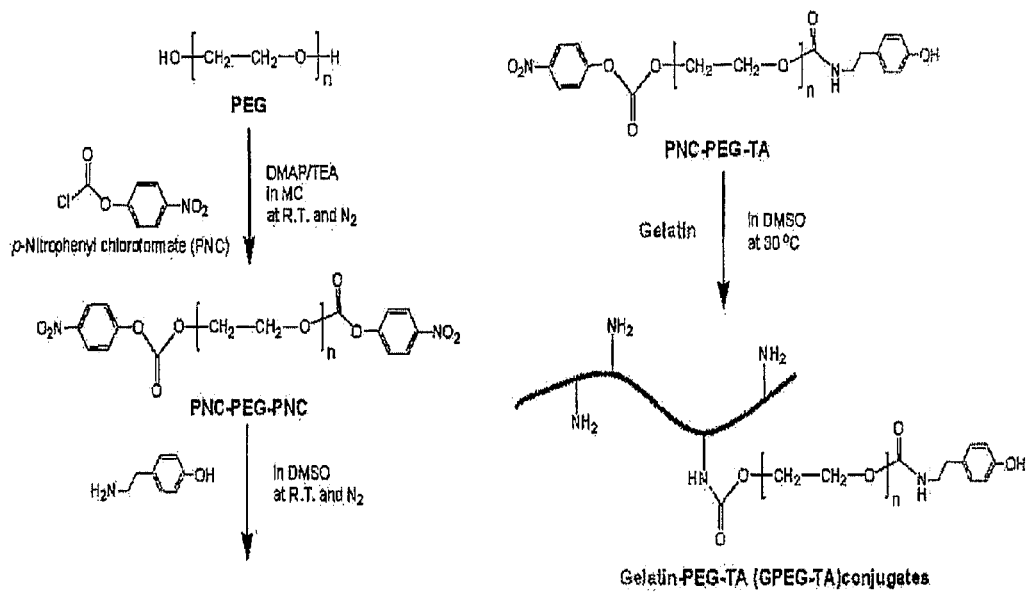
FIG. 4 is a reaction scheme showing the synthesis of a GPEG-TA copolymer.

Chemistry FIG. 3
[Chem. 3]
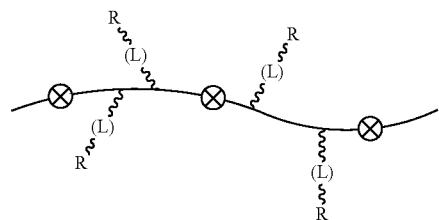
Chemistry FIG. 4
[Chem. 4]
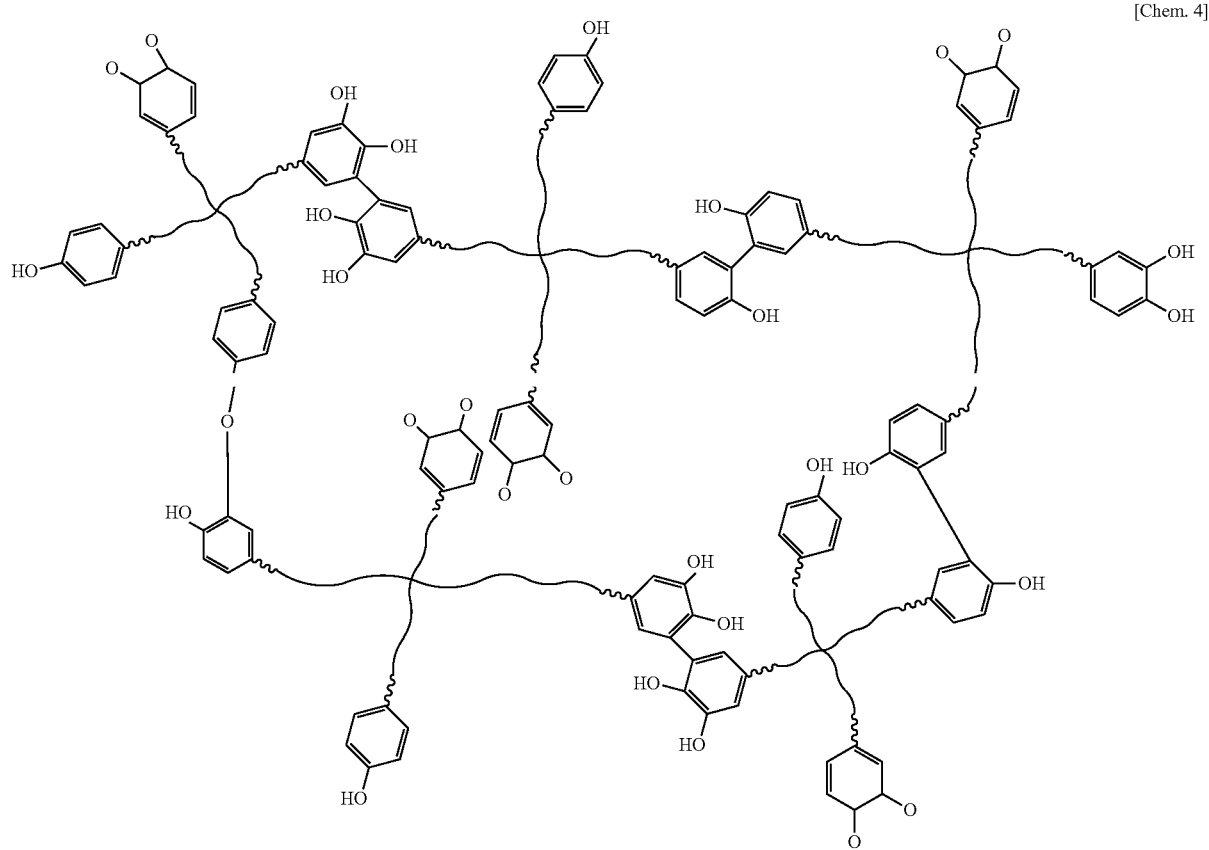

Figure 5:
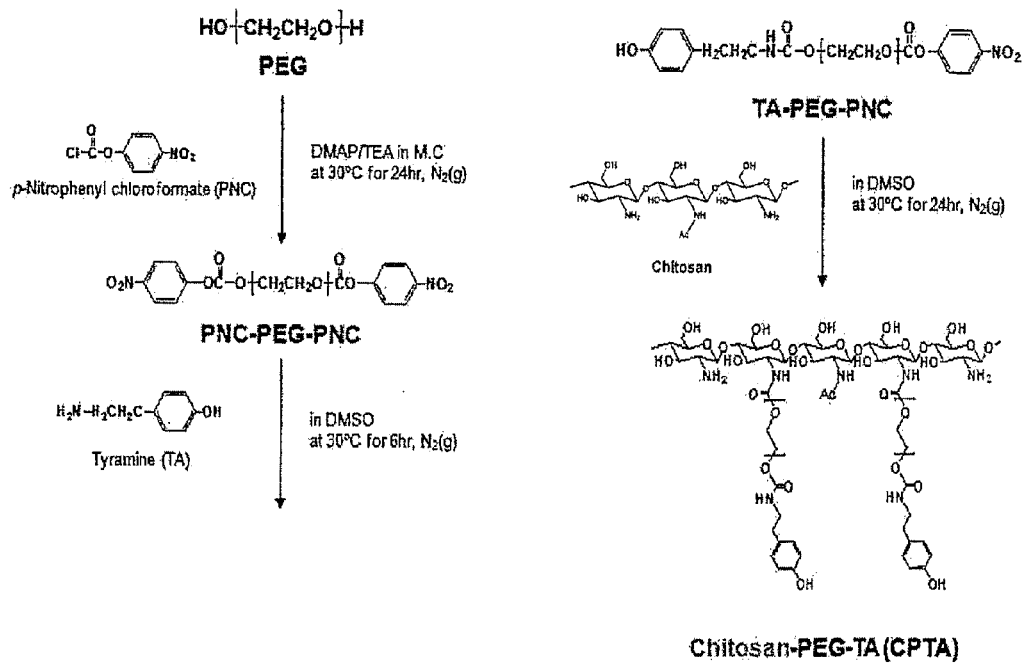
FIG. 5 is a reaction scheme showing the synthesis of a CPEG-TA copolymer.

-continued
Chemistry FIG. 5
[Chem. 5]
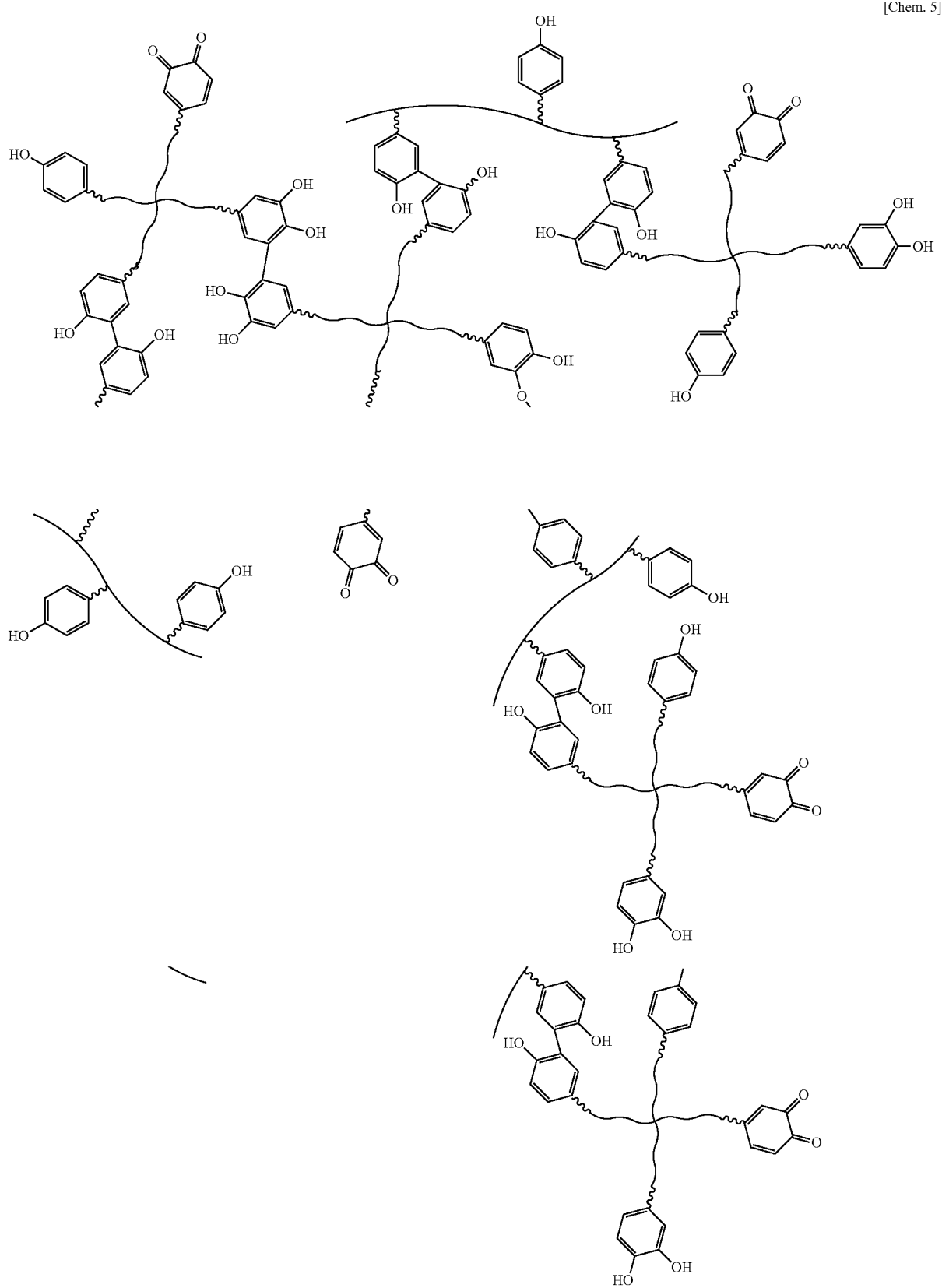

Figure 6:
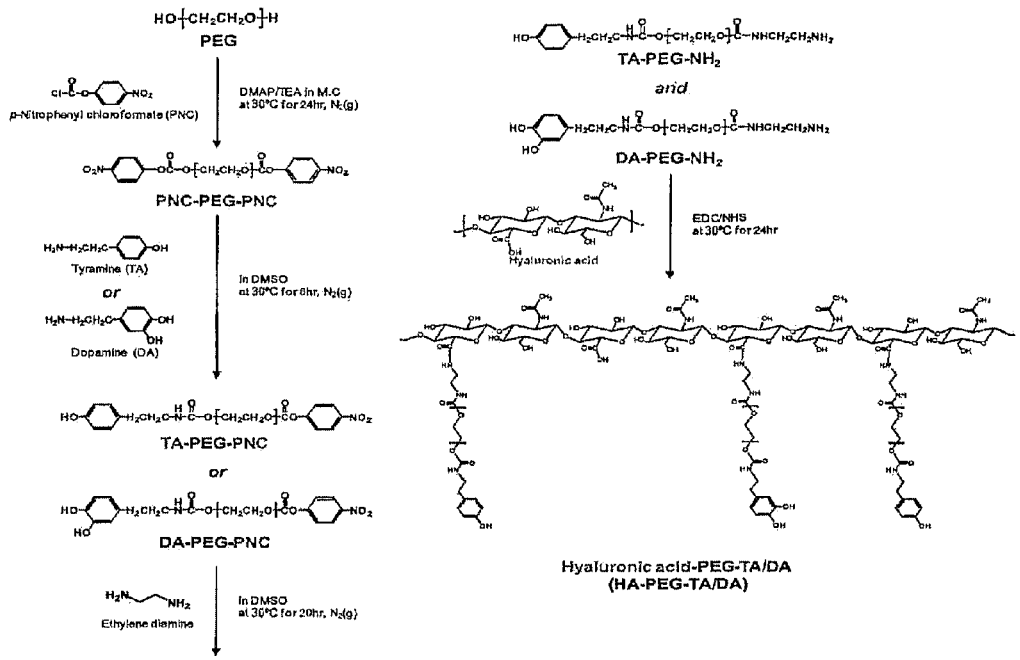
FIG. 6 is a reaction scheme showing the synthesis of an HA-PEG-TA/DA copolymer.
Figure 7:
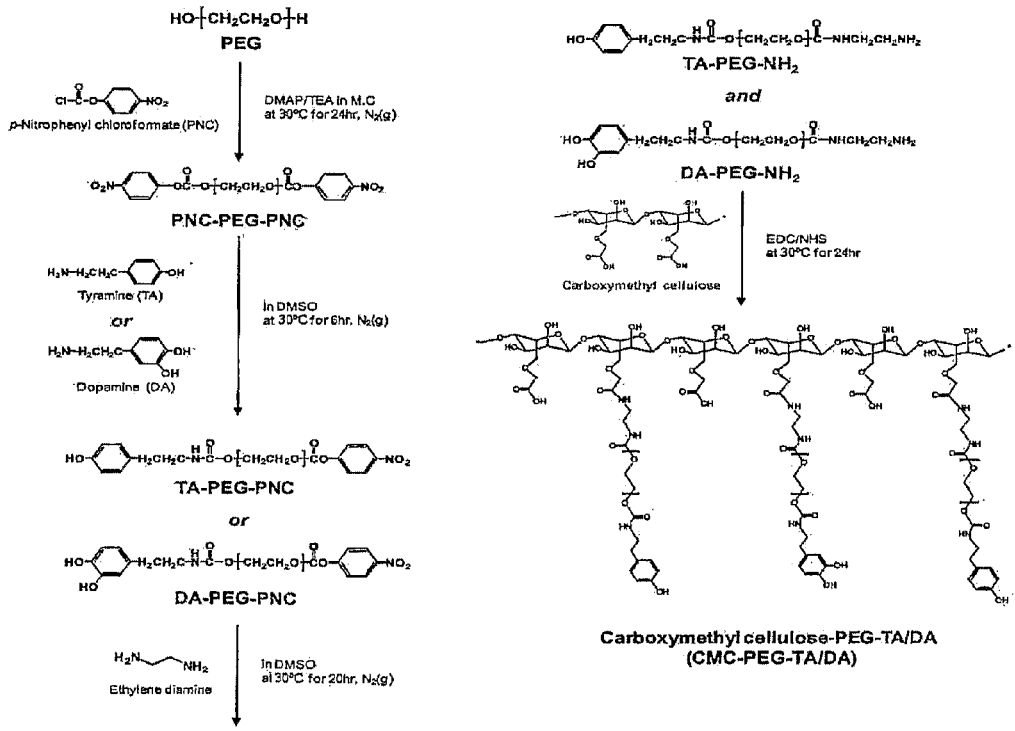
FIG. 7 is a reaction scheme showing the synthesis of a CMC-PEG-TA/DA copolymer.

-continued
Chemistry FIG. 6
[Chem. 6]
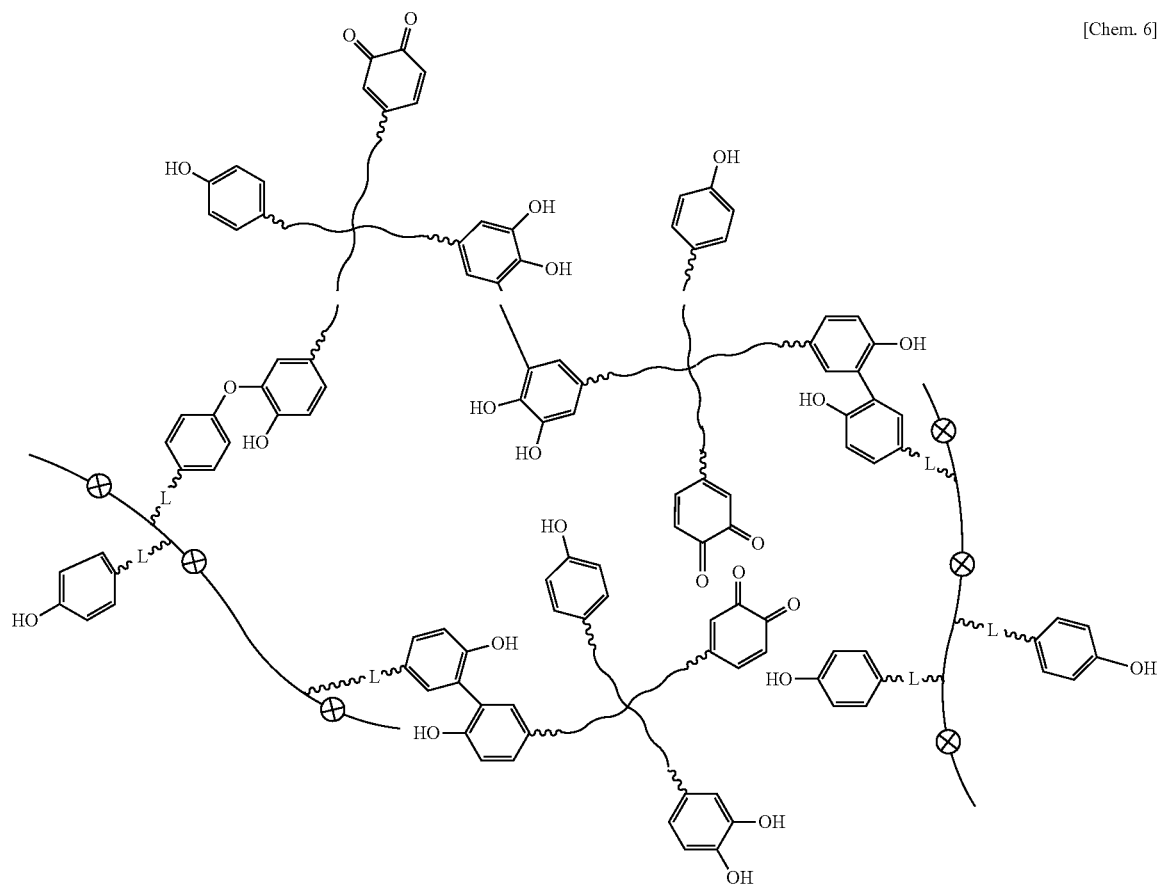
Chemistry FIG. 7
[Chem. 7]
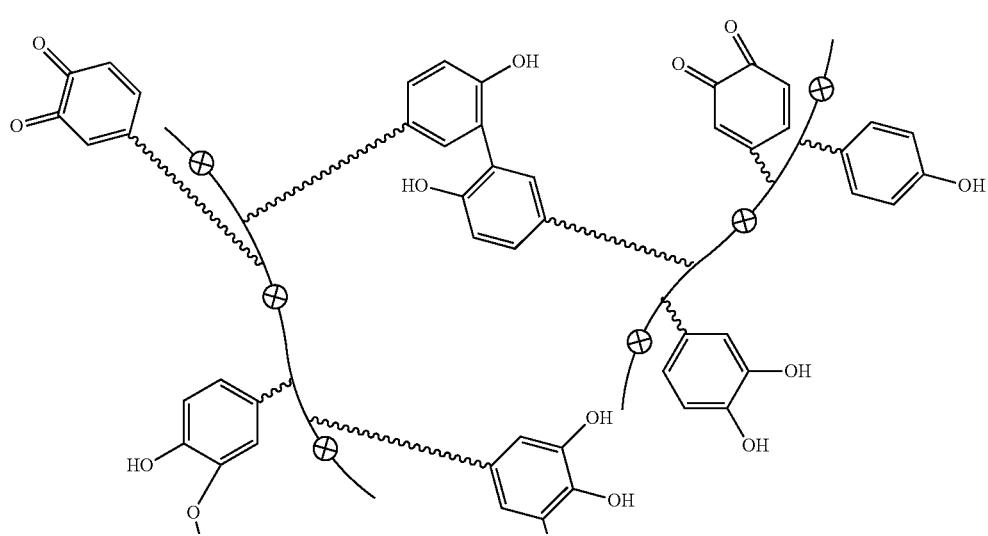

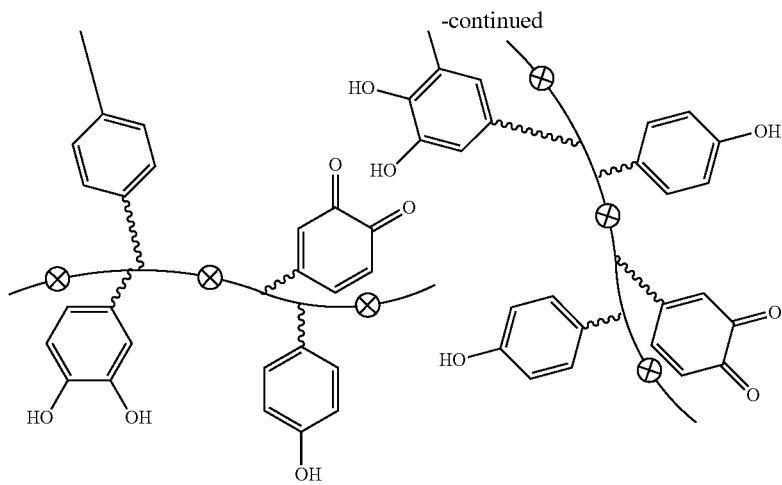

wherein,

R is a radical selected from among phenol, aniline, dopa, dopa quinone and derivatives thereof;

X is hydroxyl or amine; and

L is a polymeric linker, with (L) representing the presence or absence of the linker.

When horseradish peroxidase or hydrogen peroxide is added thereto, the polymers can be in situ cross-linked in vivo or in vitro.

The polymers of Chemical Formulas 1 to 3 may be prepared by grafting a compound selected from among phenol, aniline, dopa, dopaquinone and derivatives thereof to a polymer backbone having amino, hydroxyl or carboxyl groups through an amide, urethane, urea or ester bond, with or without a water-soluble polymer serving as a linker.

For example, the polymers of Chemical Formulas 1 to 3 can be prepared as illustrated in Reaction Schemes 1 to 13. In the reaction schemes, EDC stands for 1-ethyl-3-(3-dimethylaminopropyl)-carbodiimide, NHS for N-hydroxysuccinimide, TEA for triethylamine, DMAP for dimethylammonium pyridine, and NPCF for p-nitrophenylchloroformate.

In detail, natural or synthetic polymers having one or more functional groups selected from among hydroxyl, amine and carboxyl are modified at the functional groups with phenol, an aniline derivative or dopa/dopa quinine, with or without a water-soluble polymer serving as a linker therebetween, resulting in polymers, represented by Chemical Formula 1 to 3.

Before serving as a linker, the water-soluble polymer may be customized with succinic anhydride or NPCF, TEA and DMAP.

When the modification is achieved with a phenol derivative or an aniline derivative, both EDC and NHS may be used to activate the polymer. When a naturally occurring or synthetic polymer backbone is added, EDC and NHS may be also added in combination to activate the polymer.

In addition, when the water-soluble polymer is modified with a phenol derivative, an aniline derivative or a dopa/dopaquinine derivative, a diamine compound may be added.

[Reaction Scheme 1]

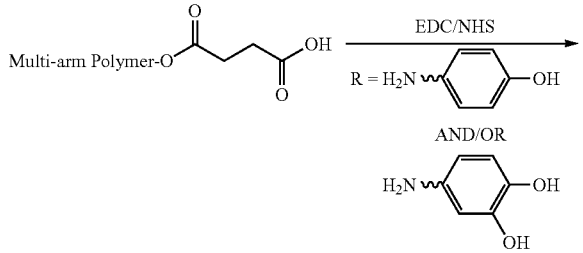

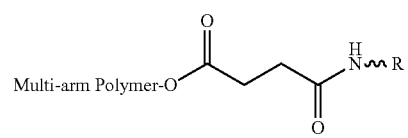

[Reaction Scheme 2]

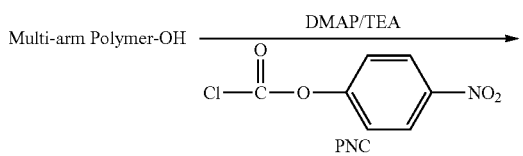

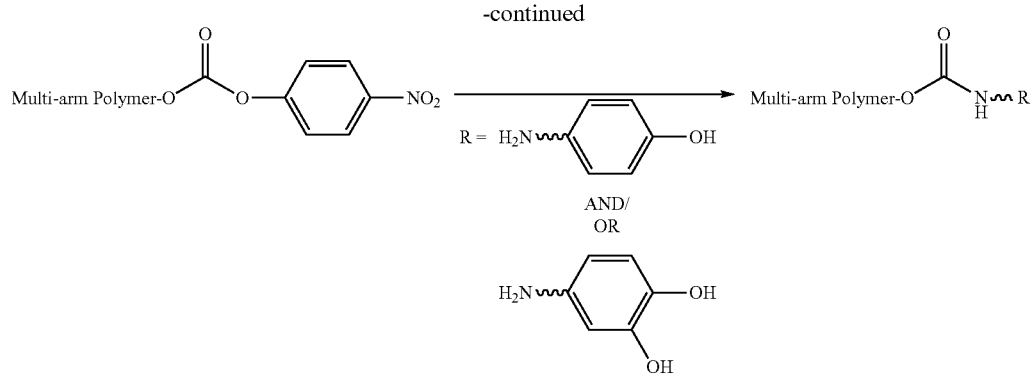
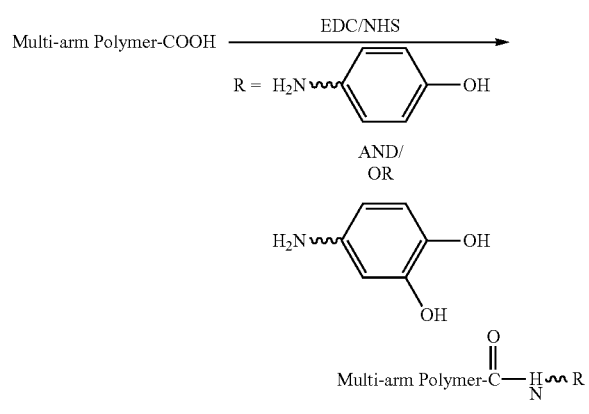
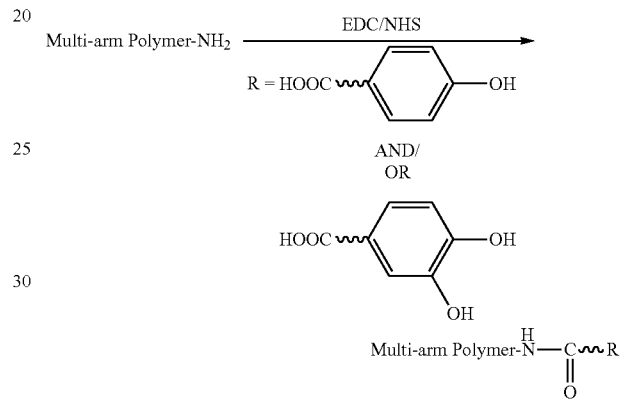
[Reaction Scheme 5]
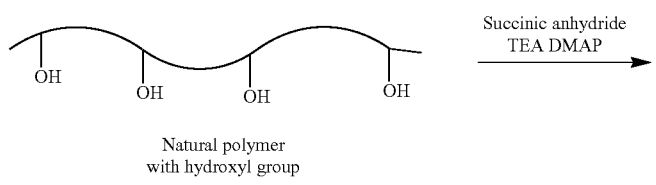
Natural polymer
with hydroxyl group
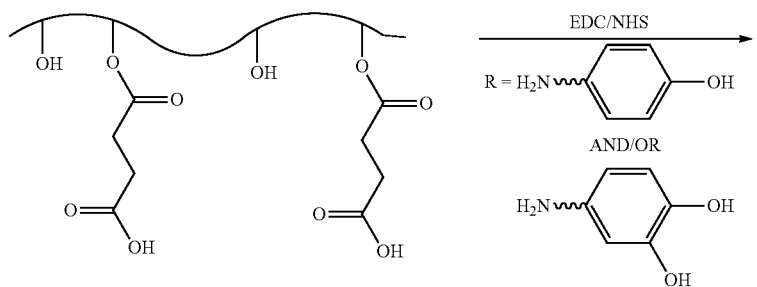

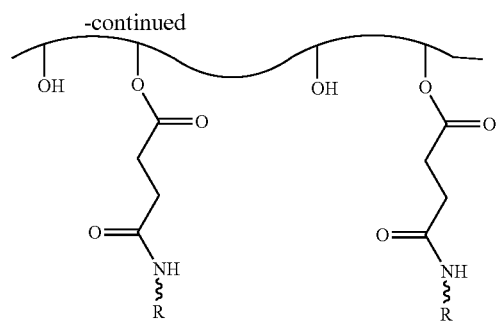
[Reaction Scheme 6]
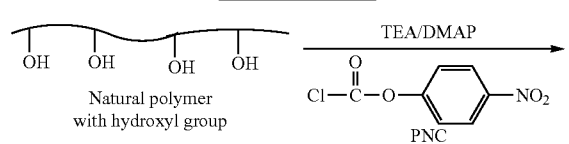
[Reaction Scheme 7]
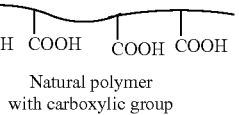 
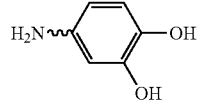
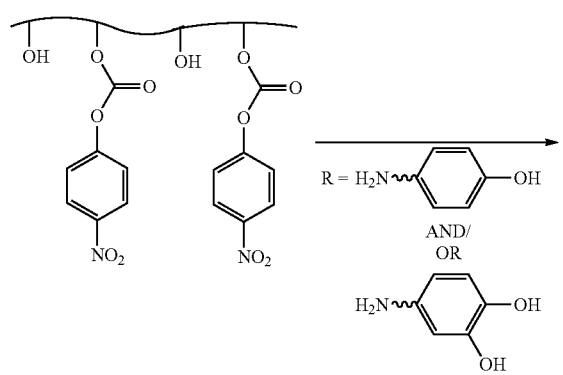
[Reaction Scheme 8]
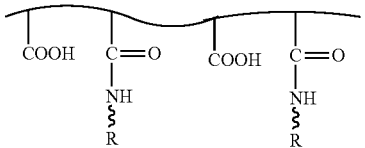
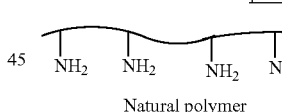 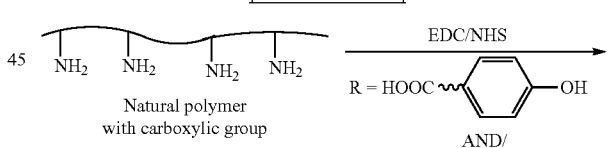
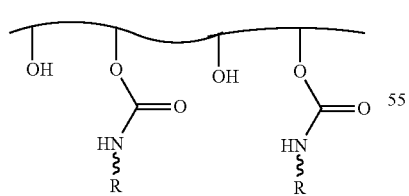 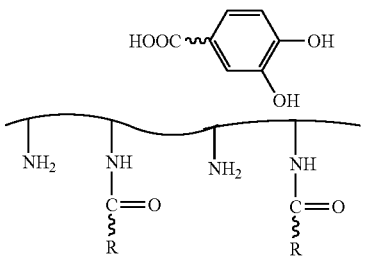
[Reaction Scheme 9]
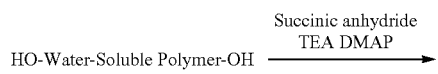

-continued
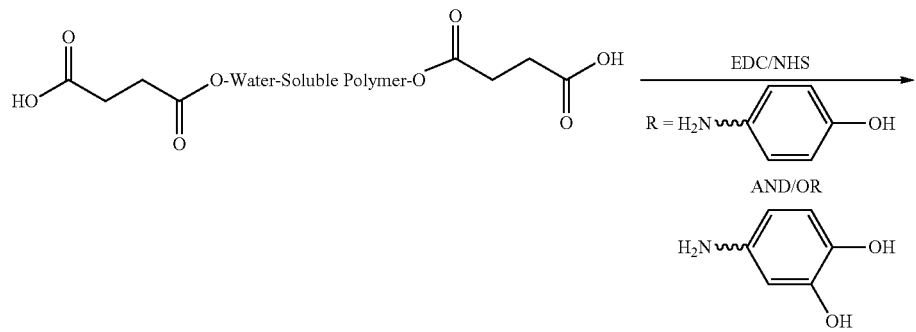
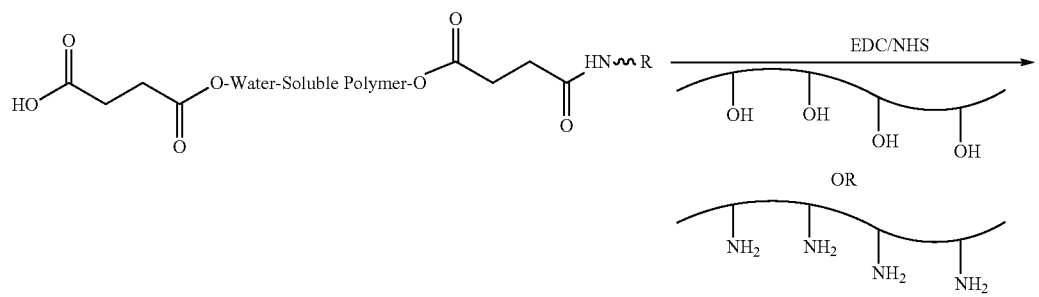
Natural polymer back bone
with hydroxyl and amine group
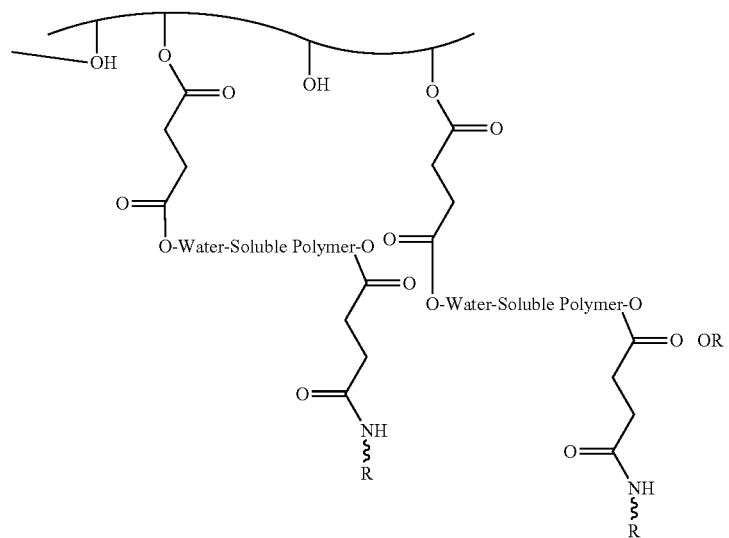

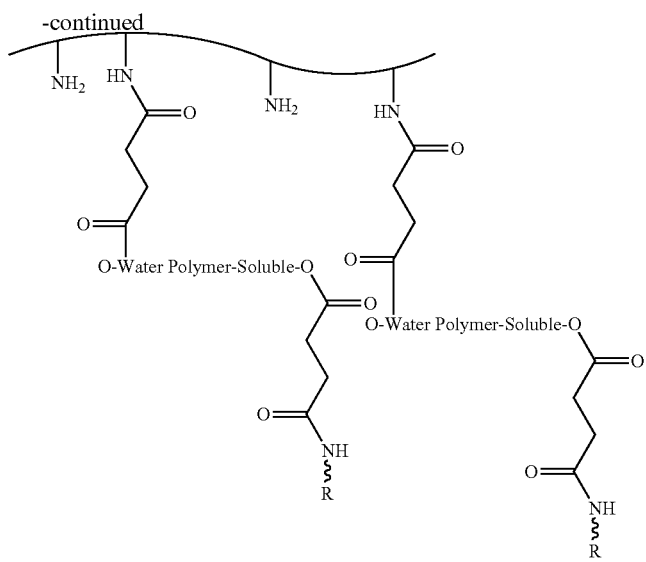
[Reaction Scheme 10]
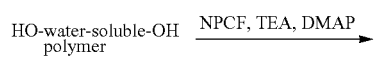
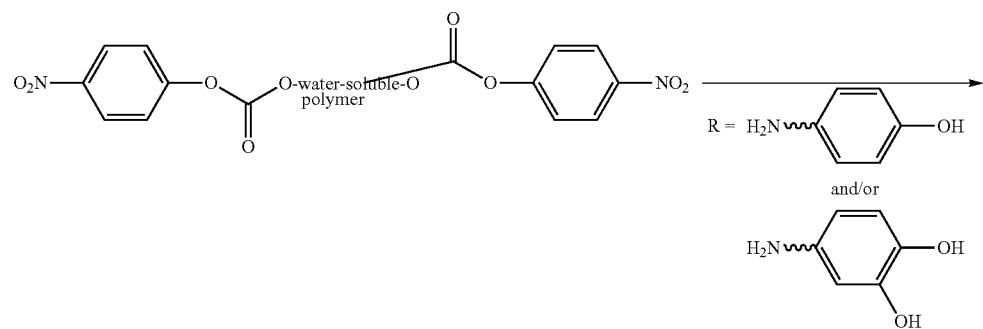
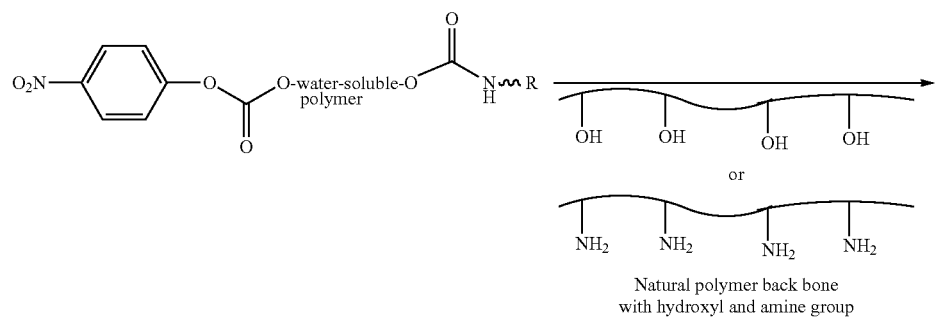
Natural polymer back bone
with hydroxyl and amine group

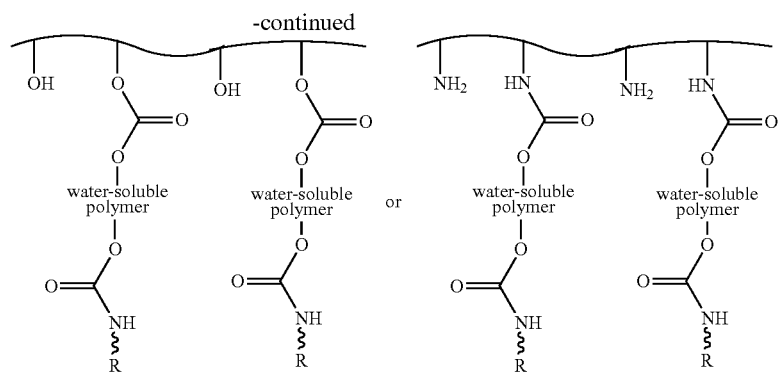
[Reaction Scheme 11]
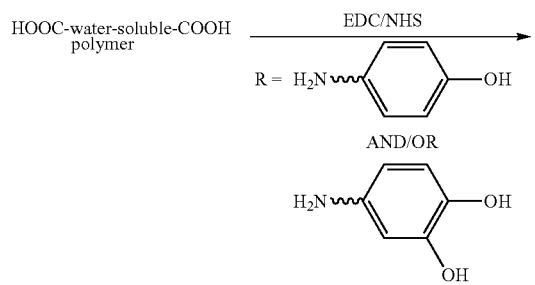
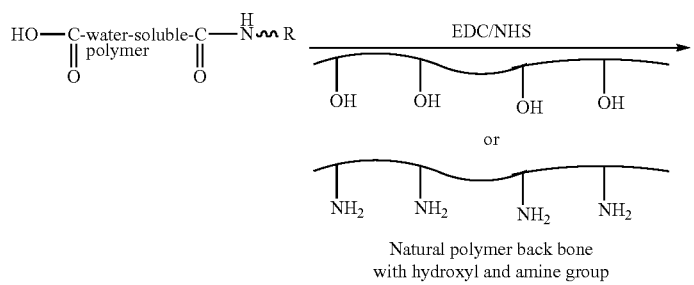
[Reaction Scheme 12]
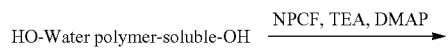

-continued
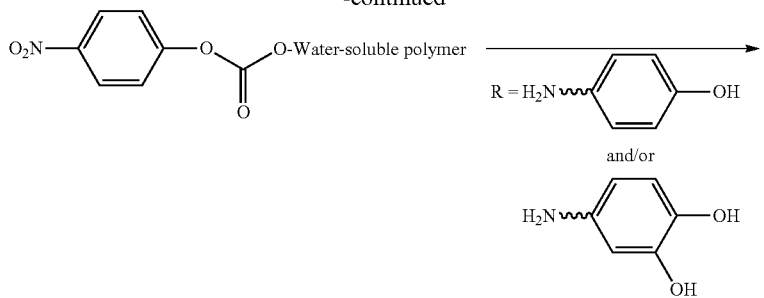
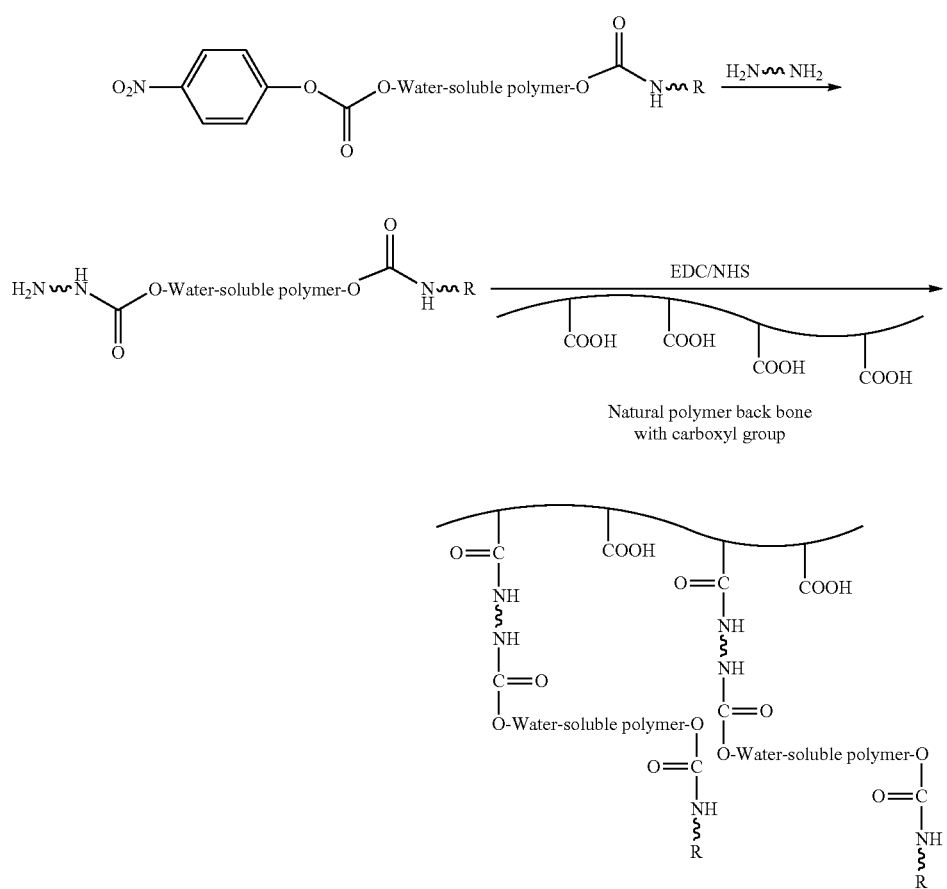
[Reaction Scheme 13]
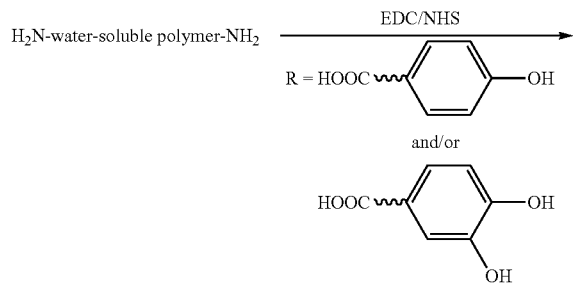

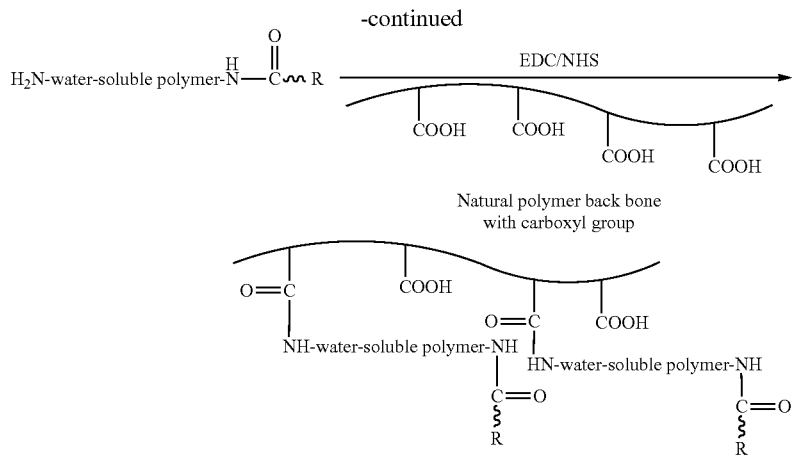

A polymer backbone suitable for use in the present invention may be selected from a group consisting of gelatin, chitosan, heparin, cellulose, dextran, dextran sulfate, chondroitin sulfate, keratan sulfate, dermatan sulfate, alginate, collagen, albumin, fibronectin, laminin, elastin, vitronectin, hyaluronic acid, fibrinogen, a multi-arm polymer and a combination thereof.

Among the multi-armed polymers suitable for use in the present invention, there are multi-arm-polyethyleneglycols such as 3-arm-polyethyleneglycol (3armPEG), 4-arm-polyethyleneglycol (4armPEG), 6-arm-polyethyleneglycol (6armPEG) and 8-arm-polyethyleneglycol (8armPEG); and the tetronic series (4arm-PPO-PEO).

The phenol derivative useful in the present invention is selected from the group consisting of tyramine, hydroxyphenylacetic acid, hydroxypropionic acid, derivatives thereof, and a combination thereof. As for the aniline derivative useful in the present invention, it is selected from the group consisting of hydroxyethylaniline, aminoethylaniline, aminobenzylalcohol, derivatives thereof, and a combination thereof. One or more compounds selected from among L-dihydroxyphenylalanine (L-DOPA), dopamine, norepinephrine, epinephrine and derivatives thereof are useful as the dopa derivative in the present invention.

One or more the water-soluble polymer used as a linker in the present invention, it may be selected from the group consisting of polycationic, polyanionic, polyamphoteric, polynonionic, polypeptide, polyaliphatic, polyaromatic, polyester, polyanhydride, polyorthoester, polyurathane, and polyamide chain. Examples of the water-soluble polymers include polyethylene glycol (PEG), polyethylene oxide (PEO), polyethylenimine (PEI), polypropylene oxide (PPO), polyvinyl alcohol (PVA), poly(N-isopropylacrylamide) (polyNIPAAM), polyfumarate, polyorganophosphazene, polyacrylic acid (polyAAc), polyacrylsulfonate, poly hydroxyethylmethacrylate (polyHEMA), and copolymers thereof, but are not limited thereto. And, examples of the copolymers include PEO-PPO-PEO (Pluronic® series), 4-arm PEO-PPO-PEO (Tetronic® series), PEG-PEI, PEG-PVA, PEG-PEI-PVA, PEI-PVA, poly(NIPAAM-co-AAc), poly(NIPAAM-co-HEMA), and combinations thereof, but are not limited thereto.

As for the water-soluble polymer used as a linker in the present invention, it may be selected from the group consisting of a hydrophilic linear or multi-arm block copolymer selected from the group consisting of polyethylene glycol (PEG)-polylactic acid (PLA), polyethylene glycol (PEG)-polycarpropactone (PCL), polyethylene glycol (PEG)-poly(DL-lactic-co-glycolic acid) (PLGA), poly((propylene)fumarate), poly((ethylene)fumarate) and combinations thereof, but is not limited thereto. The hydrogel according to the present invention can be customized in terms of physicochemical properties including gelation time, hydrogel stability (time taken to degrade), mechanical strength and water content by controlling the concentration of horseradish peroxidase and hydrogen peroxide.

In addition, the physicochemical properties of the hydrogel including gelation time, lifespan, mechanical strength and water content can be controlled with the molecular weight of the water-soluble polymer to be used.

The adhesive strength of the hydrogel is dependent on various factors including the content of dopa or derivatives thereof, and the ratio between the polymer having dopa or derivatives thereof and the polymer having phenol, aniline or derivatives thereof in a heterogeneous blend.

The hydrogel according to the present invention can be cross-linked in situ with the aid of a dual syringe kit or can be sprayed using a nozzle-mounted dual syringe kit. In addition, the hydrogel can be formed into sheets or discs using a dual syringe kit and a Teflon mold.

Further, the hydrogel according to the present invention can be in situ cross-linked with a physiologically active substance containing phenol, aniline, amine or thiol. Preferably, the physiologically active substance may be tyrosine.

In accordance with another aspect thereof, the present invention provides a tissue adhesive and hemostat comprising the in situ-forming, bioadhesive hydrogel as an active ingredient. The tissue adhesive and hemostat can be applied to various medical situations, such as cerebral nervous system surgery including vascular surgery, orthopedic surgery including bone bonding, hemostasis in patients with lacerations, closure of the femoral artery, closure after incision of an eye affected with cataract, the healing of cartilage and articular cartilage, dermal adhesion, hemostasis at incised portions in organs/secretory glands, anastomosis of gastrointestinal organs, healing of ligaments and tendons, etc.

In accordance with a further aspect thereof, the present invention provides an implant material for tissue regeneration and augmentation comprising the in situ-forming bioadhesive hydrogel as an active ingredient.

The implant material can be used in cartilage regeneration, bone regeneration, periodontal regeneration, skin regeneration, cardiac tissue regeneration, artificial intraocular lens, spinal cord regeneration, cranial regeneration, vocal regeneration and augmentation, adhesion barrier, urinary incontinence treatment, wrinkle removal, wound dressing, tissue augmentation or intervertebral disc treatment.

In accordance with still a further aspect thereof, the present invention provides a carrier for delivering biologically active materials and drugs, comprising the in situ-forming bioadhesive hydrogel as an active ingredient. The biologically active materials or drugs may be peptide or protein drugs, anti-bacterial agents, anti-cancer agents, and/or anti-inflammatory agents.

Examples of the peptide or protein drugs include fibroblast growth factor (FGF), vascular endothelial growth factor (VEGF), transforming growth factor (TGF), bone morphogenetic protein (BMP), human growth hormone (hGH), pig growth hormone (pGH), granulocyte colony-stimulating factor (G-CSF), erythropoietin (EPO), macrophage colony-stimulating factor (M-CSF), tumor necrosis factor (TNF), epidermal growth factor (EGF), platelet-derived growth factor (PDGF), interferon-$\alpha,\beta,\gamma$, interleukin-2 (IL-2), calcitonin, nerve growth factor (NGF), growth hormone releasing hormone, angiotensin, luteinizing hormone releasing hormone (LHRH), luteinizing hormone releasing hormone agonist (LHRH agonist), insulin, thyrotropin-releasing hormone (TRH), angiostatin, endostatin, somatostatin, glucagon, endorphine, bacitracin, mergain, colistin, monoclonal antibodies, and vaccines.

Examples of the anti-bacterial agents include minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, amikacin, tobramycin, dibekacin, cefotaxime, cefaclor, erythromycine, ciprofloxacin, levofloxacin, enoxacin, vancomycin, imipenem, and fusidic acid.

Examples of the anti-cancer agent include paclitaxel, taxotere, adriamycin, endostatin, angiostatin, mitomycin, bleomycin, cisplatin, carboplatin, doxorubicin, daunorubicin, idarubicin, 5-fluorouracil, methotrexate, and actinomycin-D.

Examples of the anti-inflammatory agents include acetaminophen, aspirin, ibuprofen, diclofenac, indometacin, piroxicam, fenoprofen, flubiprofen, ketoprofen, naproxen, suprofen, loxoprofen, cinnoxicam, and tenoxicam.

In an embodiment of the present invention, 4-arm-PPO-PEO (Tetronic) is conjugated with a phenol derivative and a dopa/dopa quinone derivative to synthesize Tetronic-tyramine/dopamine (Tet-TA/DA) which is then converted into in situ-forming, bioadhesive hydrogel in the presence of HRP and $H_2O_2$.

In another embodiment, gelatin or chitosan, both enzymatically degradable, natural polymers, are used as a polymer backbone to which a phenol derivative is then attached through a water-soluble polymer, e.g., PEG, as a linker, to synthesize gelatin-PEG-tyramine (GPEG-TA) or chitosan-PEG-tyramine (CPEG-TA). Alternatively, the polymer backbone, gelatin or chitosan, is conjugated with a phenol derivative without a linker to afford gelatin-hydroxyphenylacetic acid (GHPA) or chitosan-hydroxyphenylacetic acid (CHPA). These modified polymers are mixed with the previously prepared Tet-TA/DA polymer, followed by cross-linking in the presence of HRP and $H_2O_2$ to afford an in situ-forming, bioadhesive hydrogel.

Together with the hybridization of natural/synthetic polymers, the introduction of dopa/dopa quinone derivatives brings about an improvement in the mechanical strength, biocompatibility and tissue adhesiveness of the hydrogel. In addition, the PEG linker makes a contribution to the solubility, gelation time, mechanical strength and stability in the hydrogel.

In still another aspect, hyaluronic acid, carboxymethyl cellulose or alginate, all being biocompatible natural polymers, is used as a polymer backbone to which a phenol derivative and a dopa/dopa quinone derivative through a water-soluble linker such as PEG to give hyaluronic acid-PEG-tyramine/dopamine (HA-PEG-TA/DA), carboxymethyl cellulose-PEG-tyramine/dopamine (CMC-PEG-TA/DA), or alginate-PEG-tyramine/dopamine (ALG-PEG-TA/DA). In the presence of HRP and $H_2O_2$, these modified polymers may be converted into in situ-forming, bioadhesive hydrogel having excellent tissue adhesiveness.

Thanks to the PEG linker, the in situ-forming, bioadhesive hydrogel is improved in water solubility, gelation time, mechanical strength and biostability. The dopa/dopa quinone derivative contributes to excellent tissue adhesiveness.

The hydrogel according to the present invention finds a variety of applications in the biomedical field, including bioadhesives or hemostats; in situ-forming, tissue engineering scaffold; sustained release drug delivery systems for proteins, DNA, growth factors, cells, etc.; tissue augmentation; wound healing; and prevention of organ adhesion.

The in situ-forming, bioadhesive hydrogel can be used as a material for tissue sealants and hemostats. For use as a bioadhesive, a material must meet the following requirements: i) convenient to use, ii) be able to be sterilized, iii) be of the proper viscosity, iv) a low exothermal profile, v) short setting time, vi) strong adhesiveness, vii) low toxicity, viii) nontoxic to the system, ix) a proper lifespan in the body. The in situ-forming bioadhesive hydrogel according to the present invention was found to satisfy the conditions.

For example, when brought into contact with a peroxidase and hydrogen peroxide, the in situ-forming, bioadhesive hydrogels start to crosslink. This reaction, although exothermal, results in highly biocompatible products without the production of toxicity, and it takes the reaction from seconds to minutes to complete. The time period of the crosslinking reaction can be adjusted into a range of from seconds to minutes by using horseradish peroxidase.

Because it is formed not by physical crosslinking, but by chemical crosslinking, the hydrogel is excellent in mechanical strength and biostability. Based on the polymer backbone which can be enzymatically degraded, the hydrogel is biodegradable, and its biodegradability can be determined depending on the concentration of $H_2O_2$, i.e., crosslinking level, and the mixture ratio of the heterogeneous polymers.

Because it is low in viscosity, the solution of the synthesized polymer can be easily sterilized using a conventional method, e.g., by passing it through a 200 nm filter. Further, the dopa/dopa quinone derivative introduced thereinto provides the polymer with excellent bioadhesiveness.

In accordance yet another aspect of the present invention, the in situ-forming, bioadhesive hydrogel according to the present invention can be used as an artificial extracellular matrix to create a tissue engineering scaffold. A proper degradation rate is very important to adapt the hydrogel into an extracellular matrix because hydrogel, when used, may play an important role in the differentiation and growth of cells therein.

For example, gelatin is hydrolyzed specifically by matrix metalloprotenase (MMP), especially MMP-2 and MMP-9. The hydrogel matrix containing gelatin is degraded by the enzymes and then reformed into an extracellular matrix secreted by cells.

Also, when the hydrogel is used as a tissue engineering scaffold, its matrix stiffness has a large influence on the growth and differentiation of cells located inside the gel. The necessary matrix stiffness differs from one type of cells to another. For instance, osteocytes are known to grow well on stiff matrixes whereas soft tissue cells, e.g., fibroblasts, myoblasts, etc., require a soft matrix for their growth. In a system using an enzymatic reaction, the degree of crosslinking of hydrogel can be easily controlled by the quantity of hydrogen peroxide and therefore, the stiffness of hydrogel can be varied.

In accordance with still yet another aspect thereof, the present invention provides an artificial extracellular matrix comprising the in situ-forming, bioadhesive hydrogel, as a scaffold for drug delivery. For example, when tyramine is introduced thereinto, heparin that can bind physically with various growth factors allows the sustained release of growth factors (growth factor binding sites).

Phenol-modified cell adhesion peptides or proteins, for example, RGDY or YIGSR, may be used to increase cell adhesion inside the hydrogel matrix.

Thanks to the dopa quinone derivatives able to form a chemical bond with amines or thiols, biologically active materials including proteins and peptides can be easily immobilized inside the hydrogel matrix to improve the cell adhesion and activity of the matrix. Ingredients effective for cell growth and differentiation may be introduced into the hydrogel through enzymatic mechanism to prepare an in situ-forming bioadhesive, artificial ECM.

MODE FOR THE INVENTION

The in situ-forming, bioadhesive hydrogel according to the present invention was assayed in vitro and in vivo for tissue adhesiveness and hemostasis with different homogeneous or heterogeneous polymers being employed. Its physicochemical properties, such as gelation time, gel stability, swelling and mechanical strength, were determined for different heterogeneous polymer concentrations and hydrogen peroxide levels.

A better understanding of the present invention may be obtained through understood by means of the following examples which are set forth to illustrate, but are not to be construed as limiting the present invention.

Preparation Example 1

Synthesis of Tetronic-Tyramine/Dopamine (Tet-TA/DA)

FIG. 1 is a reaction scheme for synthesizing Tet-TA/DA.

1. Synthesis of Tetronic-(p-nitrophenyl chloroformate) [Tet-PNC]

A solution of 30 g (1.67 mmol) of tetronic in 300 mL of dioxin was mixed sequentially with a solution of 1.018 g (8.33 mmol) of 4-dimethylaminopyridine (DMAP) and 0.843 g (8.33 mmol) of triethylamine (TEA) in 40 mL of dioxane and a solution of 1.679 g (8.33 mmol) of p-nitrophenyl chloroformate (PNC) in 50 mL of dioxane. The molar ratio of tetronic:PNC:DMAP:TEA was 1:5:5:5. The reaction was performed at 30° C. for 24 hrs in a nitrogen atmosphere.

After completion of the reaction, remaining reagents were removed through a filter and the reaction product was concentrated using a rotary evaporator. The concentrated solution was dropwise added to 1600 mL of chilled ether to form precipitates which were then filtered.

The filtered powder was left for 24 hrs in a vacuum oven to remove the remaining organic solvents and to afford the desired compound (Tet-PNC) as a white powder.

2. Synthesis of tetronic-tyramine/dopamine (Tet-TA/DA)

To a solution of the previously prepared product Tet-PNC in 100 mL of dimethyl-sulfoxide (DMSO) were added to a solution of tyramine (TA) in 50 mL of DMSO and a solution of dopamine (DA) in 50 mL of DMSO. The molar ratios of Tet-PNC:TA:DA were employed as summarized in Table 1, below. The reaction was performed at 30° C. for 24 hrs in a nitrogen atmosphere.

After completion of the reaction, TA and DA which remained unreacted was removed by primary membrane dialysis against methanol (molecular weight cutoff 3500 Da) and completely removed by secondary membrane dialysis against acetone (molecular weight cutoff 3500 Da).

Following the dialysis, the solution was filtered, concentrated using a rotary evaporator, and added to 1600 mL of chilled ether to form precipitates. They were filtered and left for 24 hrs in a vacuum oven to produce the desired compound (Tet-TA/DA) as a white powder.

In Table 1, the name Tet-TA was given to the polymer in which the TA group was introduced into all four arms of the tetronic polymer, the name Tet-DA to the polymer in which the DA group were introduced into all four arms of the tetronic polymer, the name Tet-TA/DA I to the polymer in which three TA groups and one DA group were introduced respectively into the four arms, the name Tet-TA/DA II to the polymer in which two TA groups and two DA groups were introduced respectively into the four arms, and the name Tet-TA/DA III to the polymer in which one TA group and three DA groups were introduced respectively into the four arms. The polymers in which TA groups or DA groups were homogeneously/heterogeneously introduced into termini of the tetronic polymer were collectively named Tet-TA/DA.

TABLE 1

|  |  | Tet-PNC | TA | DA |
|---|---|---|---|---|
| Tet-TA | g | 10 | 0.321 |  |
|  | mmol | 0.556 | 2.780 |  |
|  | molar ratio | 1 | 5 |  |
| Tet-TA/DAI | g | 10 | 0.236 | 0.116 |
|  | mmol | 0.556 | 1.724 | 0.612 |
|  | molar ratio | 1 | 3.1 | 1.1 |
| Tet-TA/DAII | g | 10 | 0.160 | 0.221 |
|  | mmol | 0.556 | 1.167 | 1.167 |
|  | molar ratio | 1 | 2.1 | 2.1 |
| Tet-TA/DAIII | g | 10 | 0.084 | 0.327 |
|  | mmol | 0.556 | 0.612 | 1.724 |
|  | molar ratio | 1 | 1.1 | 3.1 |
| Tet-DA | g | 10 |  | 0.527 |
|  | mmol | 0.556 |  | 2.780 |
|  | molar ratio | 1 |  | 5 |

Preparation Example 2

Synthesis of Gelatin-Hydroxyphenylacetic Acid (GHPA)

FIG. 2 is a reaction scheme for the synthesis of GHPA.

10 Grams of gelatin was dissolved in 200 mL of 0.1 M 2-(N-morpholino)ethanesulfonic acid (MES) to prepare a solution A. Separately, 0.609 g (4 mmol) of 4-hydroxyphenylacetic acid (HPA) was dissolved in 50 mL of 0.1 M MES to give a solution B. 0.92 Grams (4.8 mmol) of 1-ethyl-3-(3-dimethylaminopropyl)-carbodiimide (EDC) and 0.276 g (2.4 mmol) of N-hydroxysuccinimide (NHS) were dissolved in respective 5 mL of 0.1 M MES. The EDC solution and the NHS solution were sequentially at intervals of 15 min to the solution B. 15 min after addition of the NHS solution, the solution B containing EDC/NHS was mixed with the solution A. The reaction was performed at 40° C. for 24 hrs.

After completion of the reaction, the reaction mixture was filtered through a syringe filter (450 nm). Then, the filtrate was subjected to membrane dialysis against distilled water (molecular weight cutoff 3500 Da) for 3~4 days, followed by freeze drying to afford GHPA as a white powder.

Preparation Example 3

Synthesis of Chitosan-Hydroxyphenylacetic Acid (CHPA)

FIG. 3 is a reaction scheme for the synthesis of CHPA.

0.644 Grams of low molecular weight chitosan with a degree of deacetylation of 75~85% was added to 80 mL of distilled water and its acidity was adjusted to a pH of 3 with 1 N HCl to form a solution. After 0.404 g (2.6 mmol) of HPA was added to the solution, its acidity was increased to a pH of 5 with 0.1 M NaOH. After the addition of 0.768 g (4 mmol) of EDC, the reaction was performed at 30° C. for 24 hrs.

When the reaction was completed, the reaction mixture was subjected to membrane dialysis against distilled water (molecular weight cutoff 3500 Da) to remove unreacted HPA. The dialyzed solution was lyophilized to produce CHPA in the form of semi-transparent non-woven fabric.

Preparation Example 4

Synthesis of Gelatin-Poly(ethyleneglycol)-Tyramine (GPEG-TA)

FIG. 4 is a reaction scheme for the synthesis of GPEG-TA.

1. Synthesis of poly(ethyleneglycol)-(p-nitrophenyl chloroformate) (PEG-PNC)

A solution of 10 g (2.9 mmol) of PEG in 100 mL of methylene chloride (MC) 100 ml was mixed sequentially with a solution of 0.779 g (6.38 mmol) of DMAP and 0.645 g (6.38 mmol) of TEA in 10 mL of MC and a solution of 1.286 g (6.38 mmol) of PNC in 50 mL of MC. The molar ratio of PEG:DMAP:TEA:PNC was 1:2.2:2.2:2.2. The reaction was performed at 30° C. for 24 hrs in a nitrogen atmosphere.

After completion of the reaction, the reaction mixture was filtered through a filter to remove unreacted reagents and then concentrated using a rotary evaporator. The concentrate was dropwise added to 1600 mL of chilled ether to form precipitates which were then filtered. The filtrate was left for 24 hrs in a vacuum oven to remove remaining organic solvents to afford the desired compound (PEG-PNC) as a white powder.

2. Synthesis of GPEG-TA

To a solution of 5 g (1.471 mmol) of PEG-PNC in 100 mL of DMSO was added a solution of 0.202 g (1.471 mmol) of TA in 50 mL of DMSO, with the molar ratio of PEG-PNC:TA being 1:1. A reaction was conducted at 30° C. for 6 hrs in a nitrogen atmosphere. Then, a gelatin solution (1 g/200 ml in DMSO) was added, followed by reaction at 30° C. for 24 hrs in a nitrogen atmosphere.

After completion of the reaction, the reaction mixture was subjected to membrane dialysis against water (molecular weight cutoff 6000-8000 Da) to remove unreacted PEG-TA. The dialyzed solution was lyophilized to produce the desired compound (GPEG-TA) as a white powder. In a $^1$H NMR spectrum, peaks appeared at 6.91-7.23 ppm which correspond to the TA substituent, confirmed the synthesis of GPEG-TA.

Preparation Example 5

Synthesis of Chitosan-Poly(ethyleneglycol)-Tyramine (CPEG-TA)

FIG. 5 is a reaction scheme for the synthesis of CPEG-TA copolymer

To a solution of 5 g (1.25 mmol) of PEG-PNC in 100 mL of DMSO 100 ml was added to a solution of 0.174 g (1.25 mmol) of TA in 50 mL of DMSO, with the molar ratio of PEG-PNC:TA being 1:1. The reaction was carried out at 30° C. for 6 hrs in a nitrogen atmosphere. Then, 0.5 g of chitosan dissolved in 50 mL of DMSO containing acetic acid (70 wt %) was added thereto in a flask, followed by reacting at 30° C. for 24 hrs in a nitrogen atmosphere.

Membrane dialysis against water (molecular weight cutoff 6000-8000 Da) removed unreacted PEG-TA from the solution. The dialyzed solution was lyophilized to afford the desired compound (CPEG-TA) as a white powder.

Preparation Example 6

Synthesis of Hyaluronic Acid-Poly(ethyleneglycol)-Tyramine/Dopamine (HA-PEG-TA/DA)

FIG. 6 is a reaction scheme for the synthesis of HA-PEG-TA/DA.

1. Synthesis of aminated poly(ethyleneglycol)-tyramine/dopamine (PTA/DA)

To a solution of 5 g (1.25 mmol) of PEG-PNC in 100 mL of MC was added to a solution of 0.174 g (1.25 mmol) of TA or 0.237 g of DA in 50 mL of MC, with the molar ratio of PEG-PNC:TA (or DA) being 1:1. A reaction was performed at 30° C. for 6 hrs in a nitrogen atmosphere. Thereafter, a solution of 2.254 g (37.5 mmol) of ethylenediamine in 50 mL of MC was added thereto, with the molar ratio of PEG-PNC:ethylenediamine being 1:30, followed by reacting at 30° C. for 24 hrs in a nitrogen atmosphere.

After the removal of remaining reagents through a filter, the reaction mixture was concentrated using a rotary evaporator. The concentrate was dropwise added to 1600 mL of chilled ether to form precipitates which were then filtered. The filtrate was left for 24 hrs in a vacuum oven to remove remaining organic solvent, yielding the desired compound (PTA/DA) as a white powder.

2. Synthesis of HA-PEG-TA/DA

1 Gram of hyaluronic acid in 300 mL of distilled water was mixed sequentially at intervals of 15 min with 1.307 g (6.82 mmol) of EDC and 0.392 g (3.41 mmol) of NHS. Then, 2.5 g (0.625 mmol) of PTA and 2.5 g (0.625 mmol) of PDA, each dissolved in 100 mL of distilled water, were added into a flask, followed by reacting at 30° C. for 24 hrs.

After the removal of the remaining reagents through a filter, the reaction mixture was subjected to membrane dialysis against water (molecular weight cutoff 6000-8000 Da) for 3~4 days. The lyophilization of the dialyzed solution produced the desired compound (HA-PEG-TA/DA) as a white powder.

Preparation Example 7

Synthesis of Carboxymethyl Cellulose-Poly(ethyleneglycol)-Tyramine/Dopamine (CMC-PEG-TA/DA)

FIG. 7 is a reaction scheme for the synthesis of CMC-PEG-TA/DA copolymer.

A solution of 1 g of carboxymethyl cellulose in 300 mL of distilled water was sequentially mixed at intervals of 15 min with 1.307 g (6.82 mmol) of EDC and 0.392 g (3.41 mmol) of NHS. After then, 2.5 g (0.625 mmol) of PTA and 2.5 g (0.625 mmol) of PDA, each dissolved in 100 mL of distilled water, were added thereto in a flask, followed by reacting at 30° C. for 24 hrs.

After removing the remaining reagents by filtering, the reaction mixture was subjected to membrane dialysis against water (molecular weight cutoff 6000-8000 Da) for 3~4 days. The lyophilization of the dialyzed solution produced the desired compound (CMC-PEG-TA/DA) as a white powder.

Preparation Example 8

Synthesis of
Alginate-Poly(ethyleneglycol)-Tyramine/Dopamine
(ALG-PEG-TA/DA)

Figure 8:
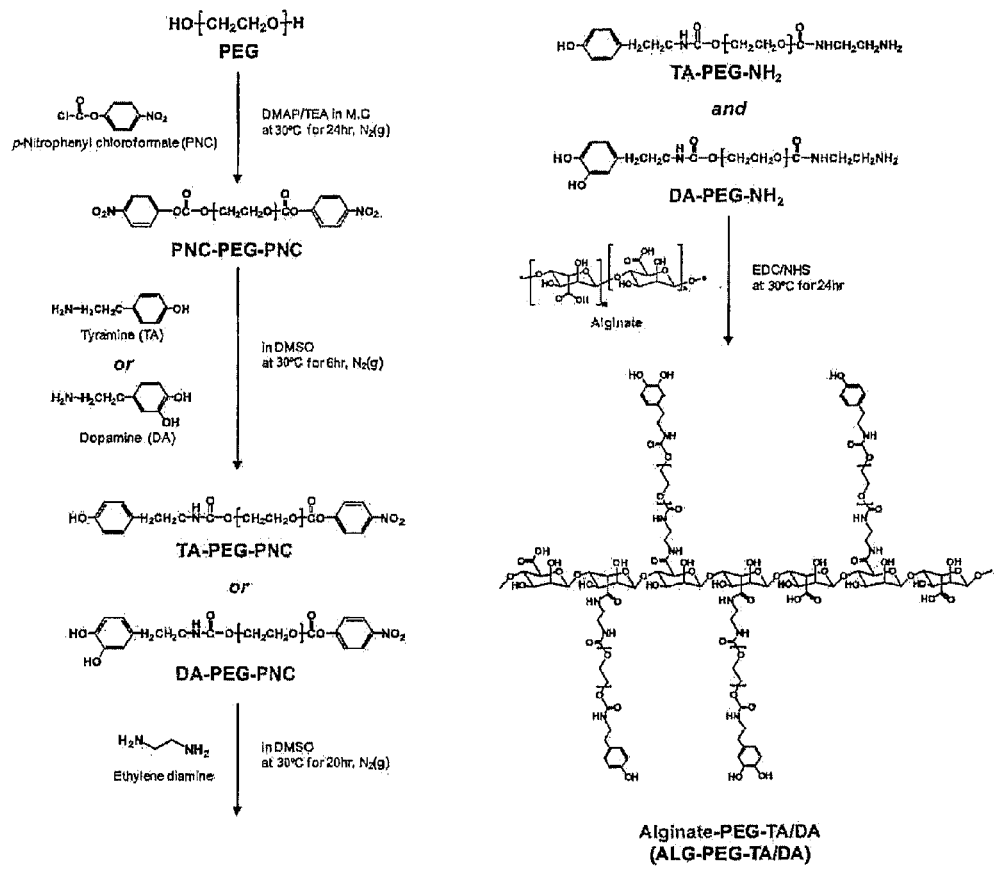
FIG. 8 is a reaction scheme showing the synthesis of an ALG-PEG-TA/DA copolymer.
Figure 9:
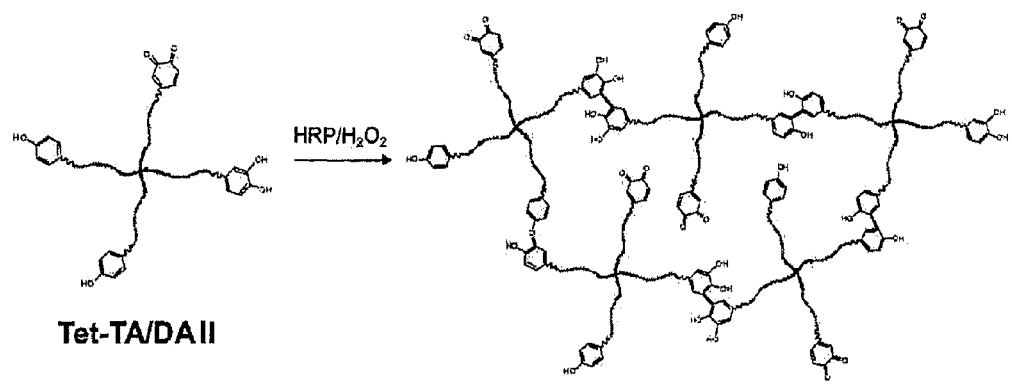
FIGS. 9 to 12 are reactions schemes showing the enzymatic preparation of an in situ-forming bioadhesive hydrogel.
Figure 10:
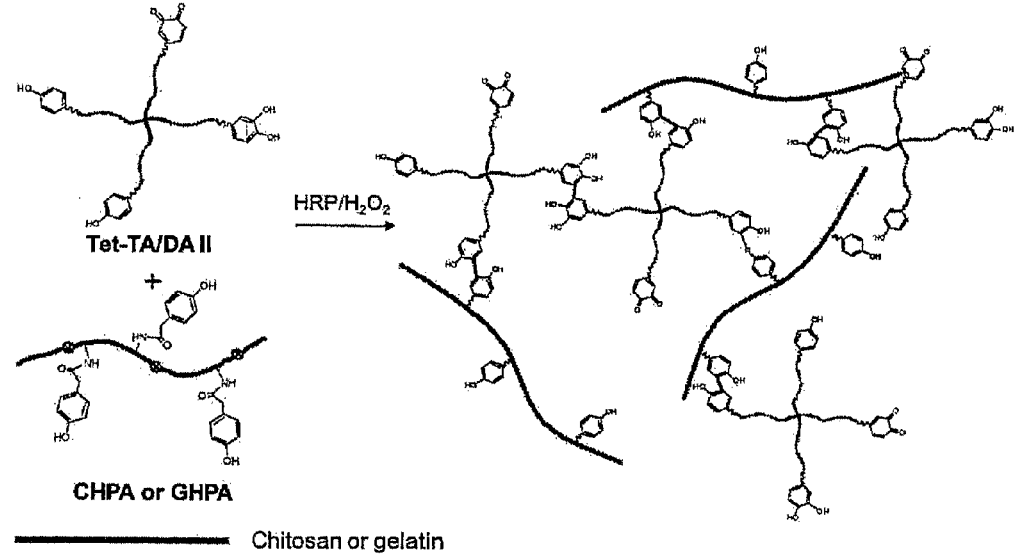
Figure 11:
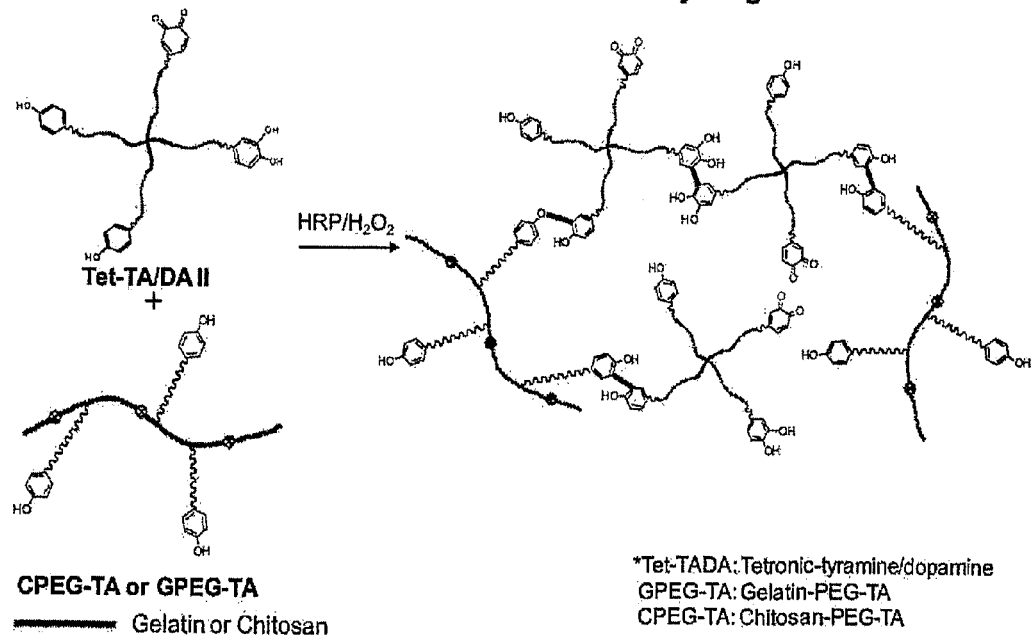
Figure 12:
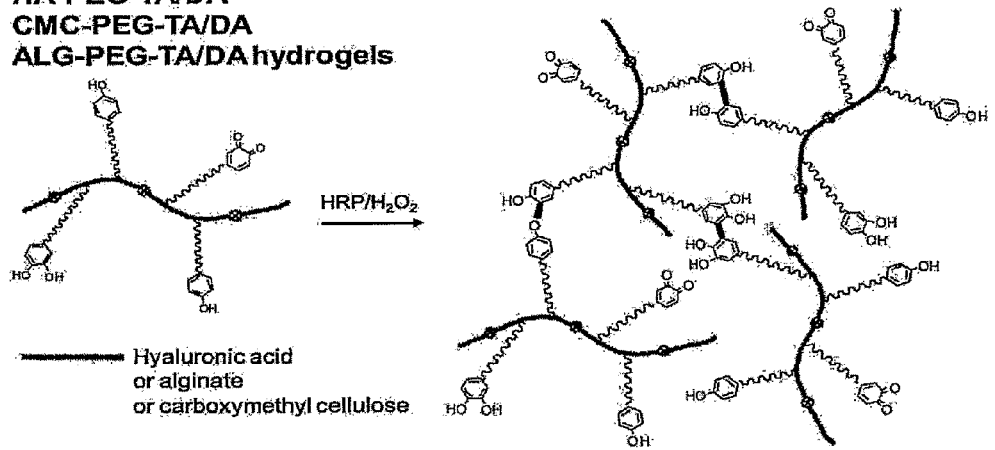

FIG. 8 is a reaction scheme for the synthesis of ALG-PEG-TA/DA copolymer.

A solution of 1 g of alginate in 300 mL of distilled water was sequentially mixed at intervals of 15 min with 1.307 g (6.82 mmol) of EDC and 0.392 g (3.41 mmol) of NHS. Then, 2.5 g (0.625 mmol) of PTA and 2.5 g (0.625 mmol) of PDA, each dissolved in 100 mL of distilled water, were added thereto in a flask, followed by reacting at 30° C. for 24 hrs.

After the removal of remaining reagents from the reaction mixture, membrane dialysis against distilled water (molecular weight cutoff 6000-8000 Da) was carried out for 3~4 days. The lyophilization of the dialyzed solution produced the desired compound (ALG-PEG-TA/DA) as a white powder.

Polymer compositions and names are summarized in Table 2, below.

TABLE 2

| Hydrogel | Polymer Composition |
|---|---|
| Tet-TA | Tet-TA |
| Tet-TA/DA I | Tet-TA/DA I |
| Tet-TA/DA II | Tet-TA/DA II |
| Tet-TA/DA III | Tet-TA/DA III |
| Tet-DA | Tet-DA |
| Tet-TA/DA II + GHPA | Tet-TA/DA II + GHPA |
| Tet-TA/DA II + CHPA | Tet-TA/DA II + CHPA |
| Tet-TA/DA II + GPEG-TA | Tet-TA/DA II + GPEG-TA |
| Tet-TA/DA II + CPEG-TA | Tet-TA/DA II + CPEG-TA |
| HA-PEG-TA/DA | HA-PEG-TA/DA |
| CMC-PEG-TA/DA | CMC-PEG-TA/DA |
| ALG-PEG-TA/DA | ALG-PEG-TA/DA |
| GPEG-TA | GPEG-TA |
| CPEG-TA | CPEG-TA |
| Tet-TA + GPEG-TA | Tet-TA + GPEG-TA |
| Tet-TA + CPEG-TA | Tet-TA + CPEG-TA |

Example 1

Preparation of Hydrogel using Enzymatic Reaction

A solution of Tet-TA/DA in HRP (solution A) was mixed with a solution of Tet-TA/DA in $H_2O_2$ (solution B) to prepare hydrogel. Separately, CPEG-TA, GPEG-TA, HA-PEG-TA/DA, CMC-PEG-TA/DA, or ALG-PEG-TA/DA were dissolved in HRP (solution A) and in $H_2O_2$ (solution B) and solutions A and B were mixed to prepare hydrogel.

The polymer solutions could be controlled to have a final concentration of from 1 to 20 wt % and to be applied in various forms using a dual syringe kit and a spray kit.

GHPA and CHPA, GPEG-TA, or CPEG-TA was dissolved in $H_2O_2$ (solution B) and mixed with a solution of Tet-TA/DA in HRP (solution A) to prepare a hydrogel.

It was possible to control the final concentrations of GHPA and CHPA in the range of from 5 to 10 wt % and from 0.05 to 1.5 wt %, respectively. At concentrations greater than these, it was practically difficult to deal with the polymer solutions due to high viscosity.

The polymers with PEG introduced thereinto, e. g., GPEG-TA, CPEG-TA, HA-PEG-TA/DA, CMC-PEG-TA/DA, and ALG-PEG-TA/DA, were highly soluble in water, and thus the polymer solutions were comparably easy to manage thanks to the low viscosity thereof.

In examples, the concentrations of hydrogel correspond to the final concentrations of the polymer which contained the hydrogel therein.

FIGS. 9 to 12 are reaction schemes showing the enzymatic preparation of in situ-forming bioadhesive hydrogel.

Example 2

Preparation of in situ-Forming Bioadhesive
Hydrogel using Dual Syringe Kit

Using a dual syringe kit, a solution of Tet-TA/DA in HRP (solution A) was mixed with a solution of GHPA, CHPA, GPEG-TA, or CPEG-TA in $H_2O_2$ (solution B) to give in situ-forming hydrogel. In this regard, solution A and solution B were placed in respective syringes. In addition, when the dual syringe kit was mounted with a nozzle, the in situ-forming bioadhesive hydrogel could be sprayed.

CPEG-TA, GPEG-TA, HA-PEG-TA/DA, CMC-PEG-TA/DA, or ALG-PEG-TA/DA was dissolved in HRP (solution A) and $H_2O_2$ (solution B) and these two solutions were mixed using the dual syringe kit, as described above, to prepare in situ-forming hydrogel.

Figure 13:
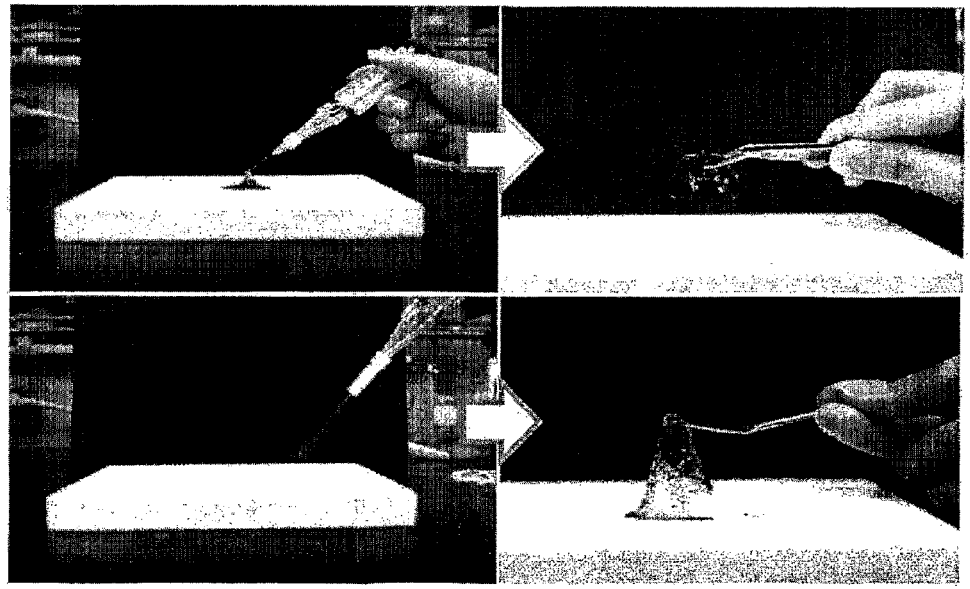
FIG. 13 is a set of photographs showing the preparation of an in situ-forming bioadhesive hydrogel using a dual syringe kit or a nozzle-mounted dual syringe kit.

FIG. 13 is a set of photographs showing the preparation of in situ-forming bioadhesive hydrogel using a dual syringe kit.

Example 3

Gelation Time of in situ-Forming Bioadhesive
Hydrogel Depending on HRP Concentration The in situ-forming bioadhesive hydrogel was evaluated for gelation time at various HRP concentrations. For this study, each polymer was dissolved in $H_2O_2$ (solution A) and in various concentrations of HRP (solution B), and the two solutions were mixed using the same quantity for each one to prepare hydrogel.

The time period taken for the mixture to cease to flow was measured using a vial tilting method and this was regarded as the gelation time of hydrogel. The gelation time was found to be controlled within the range of from 3 to 300 sec depending on the concentration of HRP. The concentration of polymer changed the gelation time by 1~8 sec. In contrast, the concentration of $H_2O_2$ had a slight influence on the gelation time.

The gelation time decreased with increasing HRP concentration because an increase in the concentration of HRP promotes the degradation of $H_2O_2$ into radicals which mediate the formation of gel. At higher polymer concentrations, there are greater numbers of the polymer chains able to form TA-TA conjugations per time. Because the polymer chains affect the formation rate of the minimal number of the networks necessary for maintaining hydrogel morphology, higher numbers of the polymer chains result in a shorter gelation time.

Figure 14:
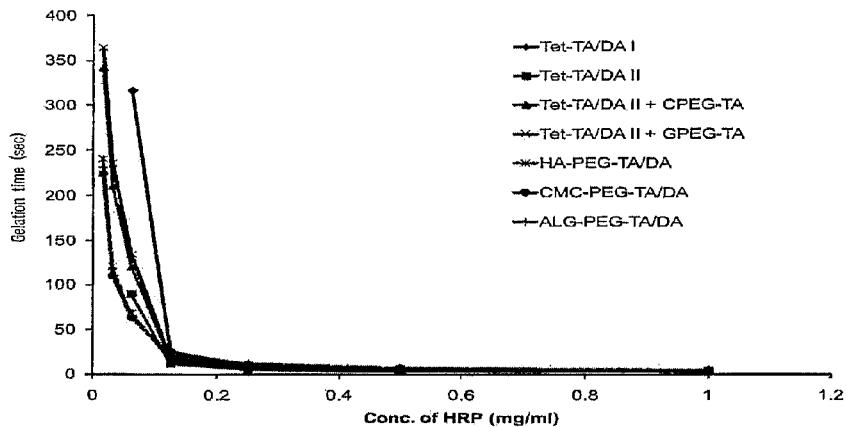
FIG. 14 is a graph showing the gelation times of an in situ-forming bioadhesive hydrogel plotted against HRP concentrations.

FIG. 14 is a graph showing the gelation times of an in situ-forming bioadhesive hydrogel plotted against HRP concentrations.

Example 4

Mechanical Strength of in situ-Forming Bioadhesive Hydrogel

Using a rheometer, Tet-TA/DAI hydrogel and Tet-TA/DAII hydrogel were measured for mechanical strength depending on polymer concentrations. Also, Tet-TA/DAII+GHPA, Tet-TA/DAII+CHPA, Tet-TA/DAII+GPEG-TA, and Tet-TA/DAII+CPEG-TA were monitored for mechanical strength while the concentrations of Tet-TA/DAII were varied.

GPEG-TA, CPEG-TA, Tet-TA/GPEG-TA, Tet-TA/CPEG-TA, HA-PEG-TA/DA, CMC-PEG-TA/DA, and ALG-PEG-TA/DA hydrogels were also evaluated for mechanical strength.

Tet-TA/DAI and Tet-TA/DAII were increased in mechanical strength from 450 Pa to 1900 Pa and from 190 Pa to 2500 Pa, respectively, with the polymer concentration changing from 5 wt % to 10 wt %. Higher mechanical strength was measured in Tet-TA/DAI at 5 wt % but in Tet-TA/DAII at 10 wt %.

This can be explained by the ratio of two factors contributing to the mechanical strength: the degree of crosslinking by TA-TA conjugation, and the coordination bond between DA and the rheometer metal surface. At a low concentration, the degree of crosslinking has a predominant influence on the mechanical strength of the hydrogel. Therefore, Tet-TA/DAI hydrogel, which contained relatively more TA groups, showed higher mechanical strength. On the other hand, coordination bonds between the DA and the rheometer metal surface make major contribution to the mechanical strength at high concentrations. Thus, Tet-TA/DAII hydrogel with relatively more DA groups has higher mechanical strength.

As the polymer concentration increased from 1 to 3 and to 5 wt %, Tet-TA/DAII+GHPA and Tet-TA/DAII+CHPA hydrogel, and Tet-TA/DAII+GPEG-TA and Tet-TA/DAII+CPEG-TA hydrogel gradually increased in mechanical strength. Depending on the kind and concentration of the polymer, the hydrogel ranged in mechanical strength from 1300 to 28500 Pa. The increase in the mechanical strength is attributed to an increase in the total polymer concentration, the degree of crosslinking with TA groups of natural polymers, and the covalent bonds between the amine groups of natural polymers and the DA groups of synthetic polymers.

Hydrogel with 5 wt % GPEG-TA and 5 wt % CPEG-TA was measured to have a mechanical strength of 2700 Pa and 6500 Pa, respectively. When mixed with 7 wt % Tet-TA, Tet-TA7+GPEG-TA5 and Tet-TA7+CPEG-TA5 hydrogel were increased in mechanical strength to 15500 Pa and 18900 Pa, respectively. A detailed description is given of the mechanical strength of in situ bioadhesive hydrogel in Table 3, below.

As seen in Table 3, in situ-forming, bioadhesive hydrogel having various mechanical strengths were prepared depending on the kind, concentration and combination of the polymers used.

TABLE 3

| Hydrogel | Composition | G' (Pa) |
| --- | --- | --- |
| Tet-TA/DAI 5 | Tet-TA/DAI 5 wt % | 450 |
| Tet-TA/DAI 10 | Tet-TA/DAI 10 wt % | 1900 |
| Tet-TA/DAII 5 | Tet-TA/DA II 5 wt % | 190 |
| Tet-TA/DAII 10 | Tet-TA/DA II 10 wt % | 2500 |
| Tet-TA/DAII1 + GHPA5 | Tet-TA/DA II 1 wt % + GHPA 5 wt % | 1300 |
| Tet-TA/DAII3 + GHPA5 | Tet-TA/DA II 3 wt % + GHPA 5 wt % | 2900 |
| Tet-TA/DAII5 + GHPA5 | Tet-TA/DA II 5 wt % + GHPA 5 wt % | 6900 |
| Tet-TA/DAII1 + CHPA1 | Tet-TA/DA II 1 wt % + CHPA 1 wt % | 1800 |
| Tet-TA/DAII3 + CHPA1 | Tet-TA/DA II 3 wt % + CHPA 1 wt % | 3700 |
| Tet-TA/DAII5 + CHPA1 | Tet-TA/DA II 5 wt % + CHPA 1 wt % | 10500 |
| Tet-TA/DAII1 + GPEG-TA5 | Tet-TA/DA II 1 wt % + GPEG-TA 5 wt % | 3300 |
| Tet-TA/DAII3 + GPEG-TA5 | Tet-TA/DA II 3 wt % + GPEG-TA 5 wt % | 8900 |
| Tet-TA/DAII5 + GPEG-TA5 | Tet-TA/DA II 5 wt % + GPEG-TA 5 wt % | 13500 |
| Tet-TA/DAII1 + CPEG-TA5 | Tet-TA/DA II 1 wt % + CPEG-TA 5 wt % | 5200 |
| Tet-TA/DAII3 + CPEG-TA5 | Tet-TA/DA II 3 wt % + CPEG-TA 5 wt % | 14000 |
| Tet-TA/DAII5 + CPEG-TA5 | Tet-TA/DA II 5 wt % + CPEG-TA 5 wt % | 28500 |
| GPEG-TA5 | GPEG-TA 5 wt % | 2700 |
| CPEG-TA5 | CPEG-TA 5 wt % | 6500 |
| Tet-TA7 + GPEG-TA5 | Tet-TA 7 wt % + GPEG-TA 5 wt % | 15500 |
| Tet-TA7 + CPEG-TA5 | Tet-TA 7 wt % + CPEG-TA 5 wt % | 18900 |
| HA-PEG-TA/DA5 | HA-PEG-TA/DA 5 wt % | 20500 |
| CMC-PEG-TA/DA5 | CMC-PEG-TA/DA 5 wt % | 19200 |
| Alginate-PEG-TA/DA5 | Alginate-PEG-TA/DA 5 wt % | 14100 |

Figure 15:
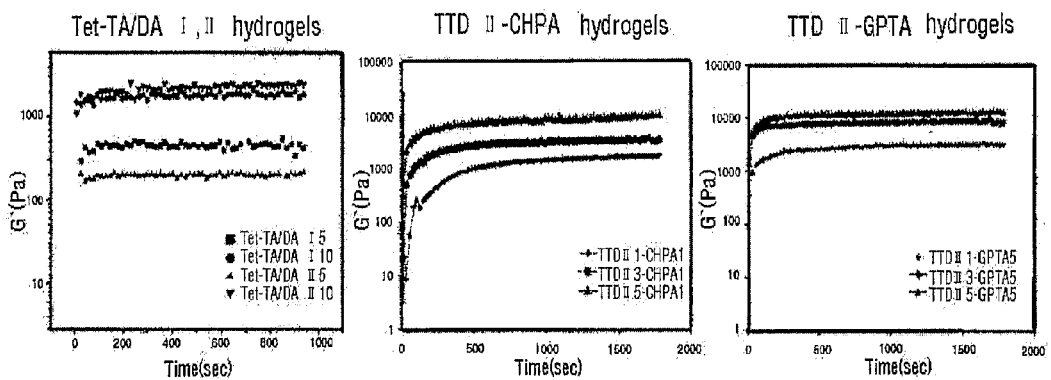
FIG. 15 is a set of graphs showing the comparison of mechanical strength between Tet-TA/DAI and II, and the change of Tet-TA/DAII+CHPA and Tet-TA/DAII+GPEG-TA hydrogel in mechanical strength with Tet-TA/DAII concentrations.

FIG. 15 is a set of graphs showing the comparison of mechanical strength between Tet-TA/DAI and II, and the change of Tet-TA/DAII+CHPA and Tet-TA/DAII+GPEG-TA hydrogel in mechanical strength with Tet-TA/DAII concentration.

Example 5

Assay for In Vitro Stability of Bioadhesive Hydrogel

The prepared bioadhesive hydrogel was assayed for stability by monitoring the hydrogel for weight and morphology from Day 0 to Day 30 while it was immersed in 0.01 M phosphate buffered saline in a 37° C. incubator. Over a one month period, Tet-TA/DAII hydrogel was maintained at a level of almost 100% in both morphology and weight, and HA-PEG-TA/DA and CMC-PEG-TA/DA hydrogel at a level of 70-80%, and Tet-TA/DAII+GPEG-TA, Tet-TA/DAII+CPEG-TA, and ALG-PEG-TA/DA hydrogel at a level of 40-60%.

Figure 16:
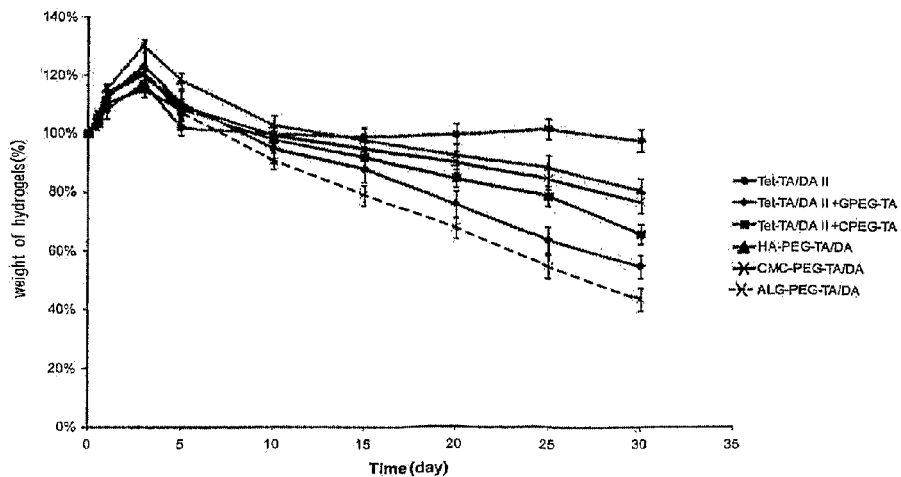
FIG. 16 is a graph showing the in vitro stability of the bioadhesive hydrogel with time.
Figure 20:
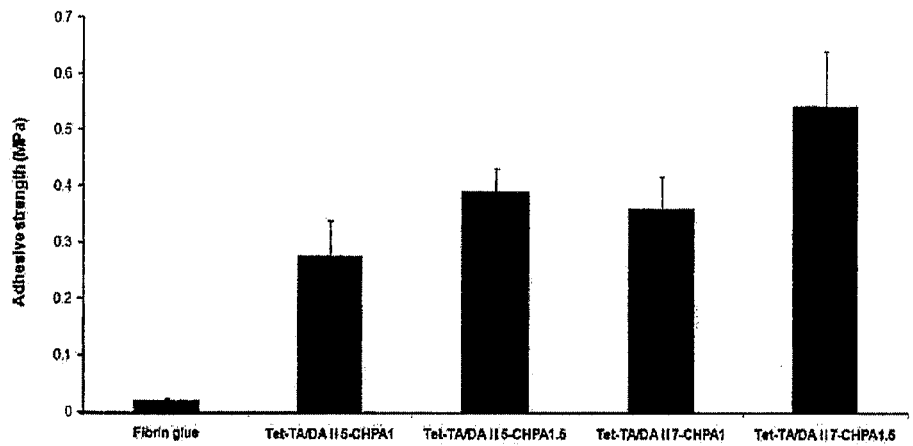
Figure 21:
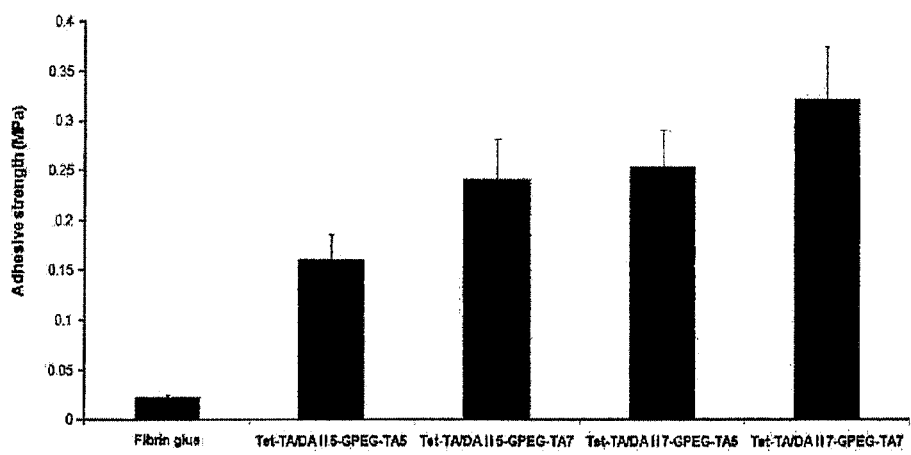
Figure 22:
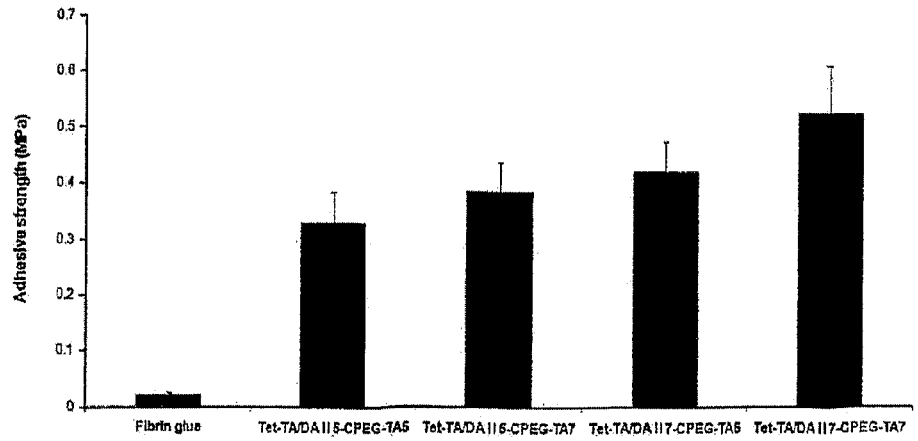
Figure 23:
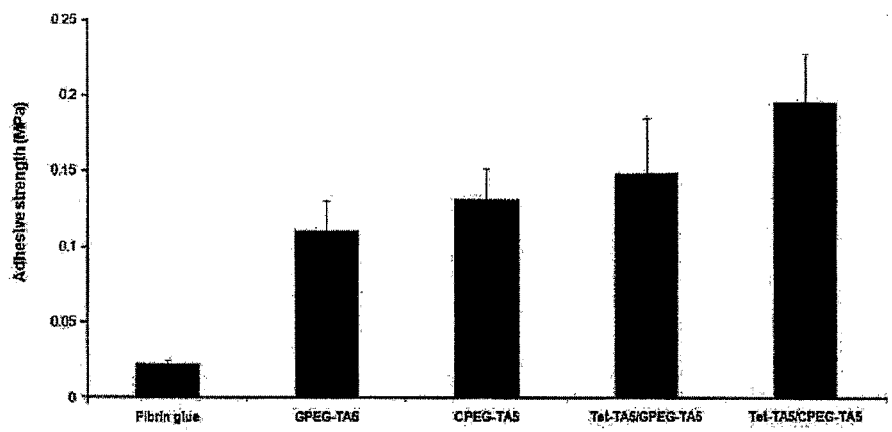
Figure 24:
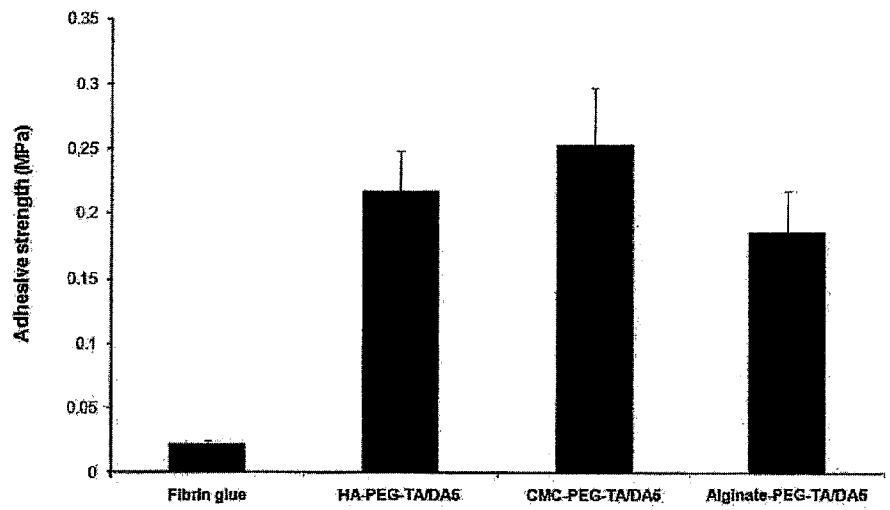

FIG. 16 is a graph showing the in vitro stability of the bioadhesive hydrogel with time.

Example 6

Biocompatibility of Hydrogel to 2D Cells

For in vitro biocompatibility assay, hydrogel discs were prepared using a Teflon mold. Osteoblasts (MC3T3-E1) were cultured at a density of $1 \times 10^4$ cells/well on the hydrogel discs to perform an assay for cytoxicity. A live/dead assay was employed in which deal and live cells were stained red and green, respectively.

The results are shown in FIG. 17. As shown in this figure, no dead cells were found in the incubated cells on the discs, demonstrating the in vitro biocompatibility of the in situ-forming, bioadhesive hydrogel.

FIG. 17 is a set of photographs showing the biocompatibility of Tet-TA/DA II, Tet-TA/DA II+GPEG-TA, Tet-TA/DA II+CPEG-TA, HA-PEG-TA/TA, CMC-PEG-TA/DA, and AGL-PEG-TA/DA hydrogel to 2D cells.

Example 7

Assay of Hydrogel for In Vitro Adhesiveness

The hydrogel was assayed for adhesiveness on pig skin using a hydraulic universal testing machine (UTM), with fibrin glue and cyanoacrylate serving as controls.

Tet-TA and Tet-TA/DA hydrogels were found to range in adhesive strength from 0.062 to 0.122 MPa, which was approximately six-fold higher compared to that of fibrin glue. With an increase in polymer concentration, the adhesive strength of Tet-TA/DAII+GHPA hydrogel increased to 0.137~0.260 MPa, which is approximately 13-fold higher than that of fibrin glue.

Tet-TA/DAII+CHPA hydrogel was measured for adhesive strength at various polymer concentrations. The hydrogel with a combination of 7 wt % Tet-TA/DAII and 5 wt % CHPA was found to have an adhesive strength of 0.544 MPa. Tet-TA/DAII7+GPEG-TA7 hydrogel and Tet-TA/DAII7+CPEG-TA7 hydrogel showed an adhesive strength of 0.325 MPa and 0.528 MPa, respectively. When mixed with a polymer containing 7 wt % Tet-TA, polymers containing 7 wt % GPEG-TA and 7 wt % CPEG-TA formed hydrogels showing an adhesive strength of 0.263 MPa and 0.310 MPa, respectively, which are higher than that of fibrin glue.

As for HA-PEG-TA/DA, CMC-PEG-TA/DA, and ALG-PEG-TA/DA hydrogels, they showed an adhesive strength of 0.218, 0.254, and 0.186 MPa, respectively, which were 8-11-fold higher than that of fibrin glue.

Depending on the kind and concentration of the polymers employed, the hydrogel can be provided with various adhesive strengths which are higher than that of fibrin glue.

TABLE 4

| Hydrogel | Composition | Adhesive Strength (MPa) |
|---|---|---|
| Fibrin glue | Fibrinogen 5 wt % | 0.023 ± 0.002 |
| Tet-TA 5 | Tet-TA 5 wt % | 0.062 ± 0.008 |
| Tet-TA 7 | Tet-TA 7 wt % | 0.080 ± 0.010 |
| Tet-TA/DA II 5 | Tet-TA/DA II 5 wt % | 0.100 ± 0.024 |
| Tet-TA/DA II 7 | Tet-TA/DA II 7 wt % | 0.122 ± 0.019 |
| Cyanoacrylate | Cyanoacrylate | 0.706 ± 0.139 |

TABLE 5

| Hydrogel | Composition | Adhesive Strength (MPa) |
|---|---|---|
| Fibrin glue | Fibrinogen 5 wt % | 0.023 ± 0.002 |
| Tet-TA/DAII5 + GHPA2.5 | Tet-TA/DA II 5 wt % + GHPA 2.5 wt % | 0.137 ± 0.014 |
| Tet-TA/DAII5 + GHPA5 | Tet-TA/DA II 5 wt % + GHPA 5 wt % | 0.200 ± 0.044 |
| Tet-TA/DAII7 + GHPA2.5 | Tet-TA/DA II 7 wt % + GHPA 2.5 wt % | 0.206 ± 0.036 |
| Tet-TA/DAII7 + GHPA5 | Tet-TA/DA II 7 wt % + GHPA 5 wt % | 0.260 ± 0.047 |
| Cyanoacrylate | Cyanoacrylate | 0.706 ± 0.139 |

TABLE 6

| Hydrogel | Composition | Adhesive Strength (MPa) |
|---|---|---|
| Fibrin glue | Fibrinogen 5 wt % | 0.023 ± 0.002 |
| Tet-TA/DAII5 + CHPA1 | Tet-TA/DA II 5 wt % + CHPA 1 wt % | 0.276 ± 0.062 |
| Tet-TA/DAII5 + CHPA1.5 | Tet-TA/DA II 5 wt % + CHPA 1.5 wt % | 0.392 ± 0.039 |
| Tet-TA/DAII7 + CHPA1 | Tet-TA/DA II 7 wt % + CHPA 1 wt % | 0.362 ± 0.056 |
| Tet-TA/DAII7 + CHPA1.5 | Tet-TA/DA II 7 wt % + CHPA 1.5 wt % | 0.544 ± 0.098 |
| Cyanoacrylate | Cyanoacrylate | 0.706 ± 0.139 |

TABLE 7

| Hydrogel | Composition | Adhesive Strength (MPa) |
|---|---|---|
| Fibrin glue | Fibrinogen 5 wt % | 0.023 ± 0.002 |
| Tet-TA/DAII5 + GPEG-TA5 | Tet-TA/DA II 5 wt % + GPEG-TA 5 wt % | 0.162 ± 0.024 |
| Tet-TA/DAII5 + GPEG-TA7 | Tet-TA/DA II 5 wt % + GPEG-TA 7 wt % | 0.243 ± 0.397 |
| Tet-TA/DAII7 + GPEG-TA5 | Tet-TA/DA II 7 wt % + GPEG-TA 5 wt % | 0.255 ± 0.038 |
| Tet-TA/DAII7 + GPEG-TA7 | Tet-TA/DA II 7 wt % + GPEG-TA 7 wt % | 0.325 ± 0.051 |
| Cyanoacrylate | Cyanoacrylate | 0.706 ± 0.139 |

TABLE 8

| Hydrogel | Composition | Adhesive Strength (MPa) |
|---|---|---|
| Fibrin glue | Fibrinogen 5 wt % | 0.023 ± 0.002 |
| Tet-TA/DAII5 + CPEG-TA5 | Tet-TA/DA II 5 wt % + CPEG-TA 5 wt % | 0.331 ± 0.053 |
| Tet-TA/DAII5 + CPEG-TA7 | Tet-TA/DA II 5 wt % + CPEG-TA 7 wt % | 0.387 ± 0.052 |
| Tet-TA/DAII7 + CPEG-TA5 | Tet-TA/DA II 7 wt % + CPEG-TA 5 wt % | 0.423 ± 0.054 |
| Tet-TA/DAII7 + CPEG-TA7 | Tet-TA/DA II 7 wt % + CPEG-TA 7 wt % | 0.528 ± 0.084 |
| Cyanoacrylate | Cyanoacrylate | 0.706 ± 0.139 |

TABLE 9

| Hydrogel | Composition | Adhesive Strength (MPa) |
|---|---|---|
| Fibrin glue | Fibrinogen 5 wt % | 0.023 ± 0.002 |
| GPEG-TA5 | GPEG-TA 5 wt % | 0.111 ± 0.019 |
| CPEG-TA5 | CPEG-TA 5 wt % | 0.143 ± 0.024 |
| Tet-TA5 + GPEG-TA5 | Tet-TA 5 wt % + GPEG-TA 5 wt % | 0.263 ± 0.045 |
| Tet-TA5 + CPEG-TA5 | Tet-TA 5 wt % + CPEG-TA 5 wt % | 0.310 ± 0.036 |
| Cyanoacrylate | Cyanoacrylate | 0.706 ± 0.139 |

TABLE 10

| Hydrogel | Composition | Adhesive Strength (MPa) |
|---|---|---|
| Fibrin glue | Fibrinogen 5 wt % | 0.023 ± 0.002 |
| HA-PEG-TA/DA5 | HA-PEG-TA/DA 5 wt % | 0.218 ± 0.031 |
| CMC-PEG-TA/DA5 | CMC-PEG-TA/DA 5 wt % | 0.254 ± 0.043 |
| ALG-PEG-TA/DA5 | ALG-PEG-TA/DA 5 wt % | 0.186 ± 0.031 |
| Cyanoacylate | Cyanoacrylate | 0.706 ± 0.139 |

FIGS. 18 to 24 are graphs showing adhesive strengths of the hydrogels Tet-TA and Tet-TA/DA II (A), Tet-TA/DAII+GHPA (B), Tet-TA/DAII+CHPA (C), Tet-TA/DAII+GPEG-TA (D), Tet-TA/DAII+CPEG-TA (E), GPEG-TA, CPEG-TA, Tet-TA+GPEG-TA, Tet-TA+CPEG-TA (F), and HA-PEG-TA/DA, CMC-PEG-TA/DA, ALG-PEG-TA/DA (G), with fibrin glue and cyanoacrylate serving as controls.

Example 8

Assay of Hydrogel for In Vivo Adhesiveness

Tet-TA, Tet-TA/DAII, Tet-TA/DAII+CHPA, and Tet-TA/DAII+GPEG-TA hydrogels were assayed for adhesiveness using white rabbits. In this regard, a dual syringe kit with a solution of Tet-TA or Tet-TA/DAII in HRP (solution A) contained in one syringe and an $H_2O_2$ solution or a solution of CHPA or GPEG-TA in $H_2O_2$ (solution B) contained in the other syringe was prepared. 5-cm long incision wounds were made on the back of white rabbits. The kit was used to close the incisions. For comparison, some of the incisions were closed with sutures.

It took 10 min to completely close the incisions with sutures. On the other hand, within 1 min after application to the incisions from the dual syringe kit, the polymer solutions were gelled to close the wounds. 10 min after wound closure, the incisions which had been treated with Tet-TA hydrogel started to open, but the incisions which had been treated with Tet-TA/DAII, Tet-TA/DAII+CHPA, Tet-or TA/DAII+GPEG-TA hydrogel remained closed.

From the assay, the data together demonstrate that Tet-TA/DAII hydrogel or hydrogel in which a Tet-TA/DAII polymer is hybridized with a naturally occurring polymer can be used as an effective bioadhesive.

Figure 25:
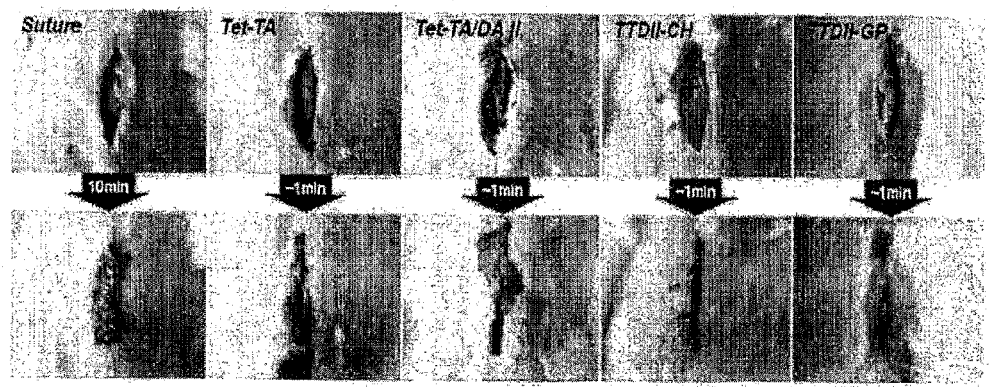
FIG. 25 is a set of photographs showing in vivo adhesiveness of Tet-TA, Tet-TA/DAII, Tet-TA/DAII+CHPA, and Tet-TA/DAII+GPEG-TA hydrogels.

FIG. 25 is a set of photographs showing the in vivo adhesiveness of Tet-TA, Tet-TA/DAII, Tet-TA/DAII+CHPA, and Tet-TA/DAII+GPEG-TA hydrogels.

Example 9

Assay of Hydrogel for In Vivo Hemostasis

Tet-TA, Tet-TA/DAII, Tet-TA/DAII+CHPA, and Tet-TA/DAII+GPEG-TA hydrogels were assayed for hemostasis using white rabbits. In this regard, a dual syringe kit was prepared in the same manner as in the adhesiveness assay. 5-cm long incision wounds were made on the back of white rabbits. The kit was used to close the incisions. 10 min after the wound closure, gauze was directly pressed against the wound. Bloodstains on the gauze were examined with the naked eye.

The bloodstains on the gauze decreased in the following order: Tet-TA>Tet-TA/DAII>>Tet-TA/DAII+GPEG-TA Tet-TA/DAII+CHPA. Particularly, almost no bloodstains were found in the regions to which the Tet-TA/DAII+CHPA hydrogel or the Tet-TA/DAII+GPEG-TA hydrogel had been applied. When adhesiveness is taken into consideration, the hydrogels which have higher adhesive strength are thought to more completely close wounds, thereby showing better hemostasis.

Figure 26:
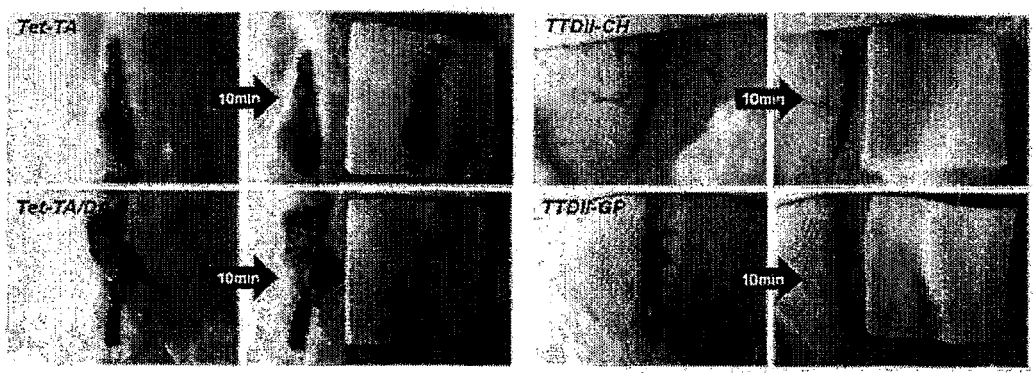
FIG. 26 is a set of photographs showing the in vivo hemostasis of Tet-TA, Tet-TA/DAII, Tet-TA/DAII+CHPA, and Tet-TA/DAII+GPEG-TA hydrogels.

FIG. 26 is a set of photographs showing the in vivo hemostasis of Tet-TA, Tet-TA/DAII, Tet-TA/DAII+CHPA, and Tet-TA/DAII+GPEG-TA hydrogels.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An in situ-forming, bioadhesive hydrogel, comprising a polymer represented by Chemical Formula 6

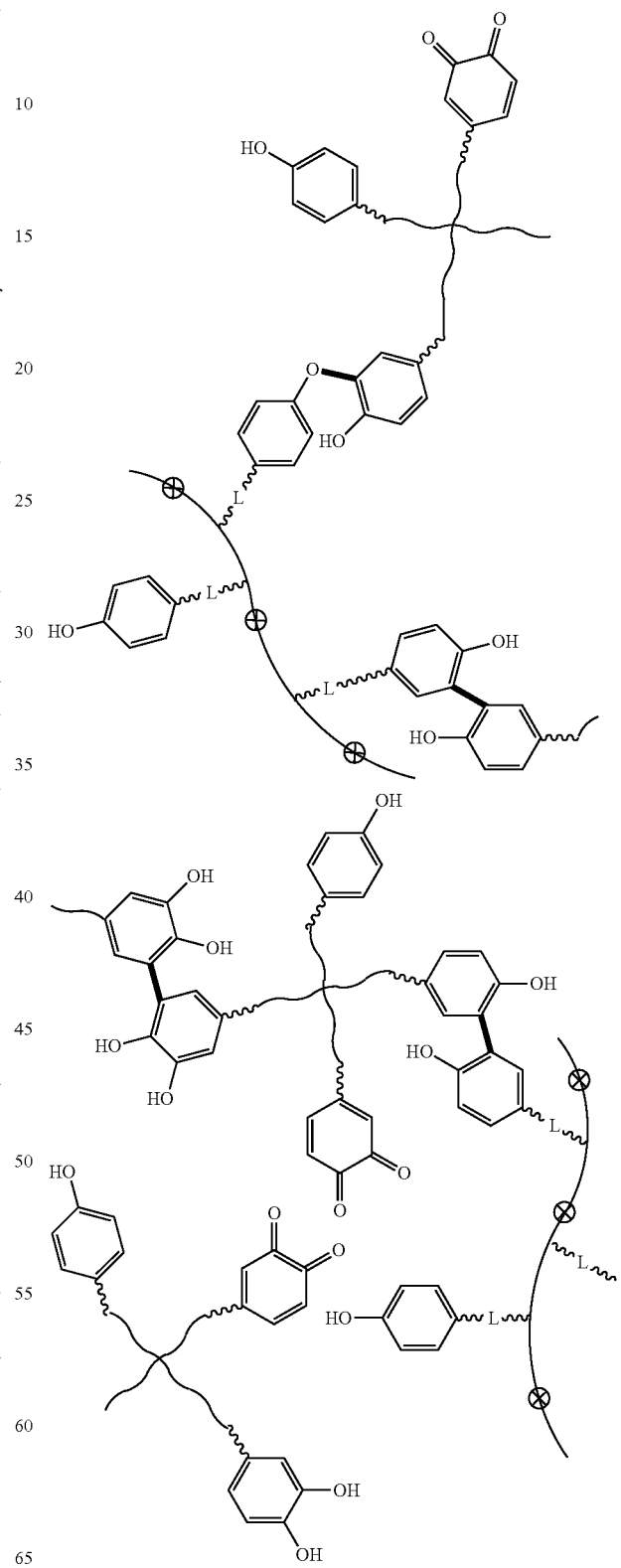

-continued

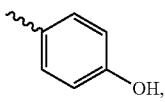

wherein the Chemical Formula 6 is a heterogeneous blend which includes i) a star-shaped polymer represented by Tet-TA/DAII having two TA groups and two DA groups

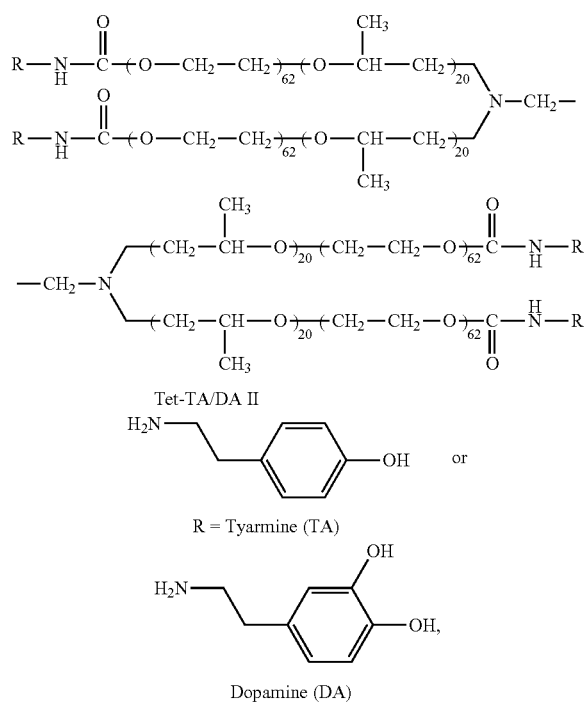

and ii) a branched polymer represented by Gelatin-PEG-TA

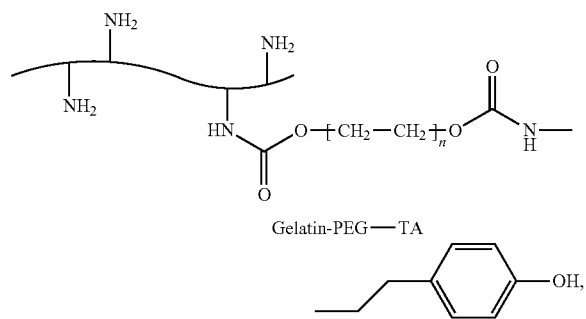

wherein the branched polymer includes a curved line representing a gelatin polymer backbone.

2. The in situ-forming, bioadhesive hydrogel according to claim 1, wherein the polymer is in situ crosslinked in vivo or in vitro when horseradish peroxidase and hydrogen peroxide are added thereto.

3. The in situ-forming, bioadhesive hydrogel according to claim 1, wherein a physicochemical property of the hydrogel is adjusted with concentrations of horseradish peroxidase and hydrogen peroxide, said physicochemical property being selected from gelation time, gel stability, mechanical strength and water content.

4. The in situ-forming, bioadhesive hydrogel according to claim 1, wherein a physicochemical property of the hydrogel is adjusted by changing a molecular weight of the water-soluble polymer, said physicochemical property being selected from gelation time, gel stability, mechanical strength and water content.

5. The in situ-forming, bioadhesive hydrogel according to claim 1, wherein an adhesive strength of the hydrogel is adjusted by changing a content of dopa or a derivative thereof, or a mixture ratio between a polymer having dopa or a derivative thereof and a polymer having phenol, aniline or a derivative thereof in the heterogeneous mixture.

6. A carrier for delivering a biologically active substance or drug, comprising the in situ-forming, bioadhesive hydrogel of claim 1.

7. The carrier according to claim 6, wherein the biologically active substance or drug is selected from the group consisting of a peptide or protein drug, an antibacterial agent, an anti-cancer agent, an anti-inflammatory agent, and a combination thereof.

8. The carrier according to claim 7, wherein the peptide or protein drug is selected from the group consisting of fibroblast growth factor (FGF), vascular endothelial growth factor (VEGF), transforming growth factor (TGF), bone morphogenetic protein (BMP), human growth hormone (hGH), pig growth hormone (pGH), granulocyte colony-stimulating factor (G-CSF), erythropoietin (EPO), macrophage colony-stimulating factor (M-CSF), tumor necrosis factor (TNF), epidermal growth factor (EGF), platelet-derived growth factor (PDGF), interferon-α,β,γ, interleukin-2 (IL-2), calcitonin, nerve growth factor (NGF), growth hormone releasing hormone, angiotensin, luteinizing hormone releasing hormone (LHRH), luteinizing hormone releasing hormone agonist (LHRH agonist), insulin, thyrotropin-releasing hormone (TRH), angiostatin, endostatin, somatostatin, glucagon, endorphine, bacitracin, mergain, colistin, monoclonal antibodies, vaccines, and a combination thereof.

9. The carrier according to claim 7, wherein the antibacterial agent is selected from the group consisting of minocycline, tetracycline, ofloxacin, fosfomycin, mergain, profloxacin, ampicillin, penicillin, doxycycline, thienamycin, cephalosporin, nocardicin, gentamicin, neomycin, kanamycin, paromomycin, micronomicin, amikacin, tobramycin, dibekacin, cefotaxime, cefaclor, erythromycine, ciprofloxacin, levofloxacin, enoxacin, vancomycin, imipenem, fusidic acid and a combination thereof.

10. The carrier according to claim 7, wherein the anti-cancer agent is selected from the group consisting of paclitaxel, taxotere, adriamycin, endostatin, angiostatin, mitomycin, bleomycin, cisplatin, carboplatin, doxorubicin, daunorubicin, idarubicin, 5-fluorouracil, methotrexate, actinomycin-D and a combination thereof.

11. The carrier according to claim 7, wherein the anti-inflammatory agent is selected from the group consisting of acetaminophen, aspirin, ibuprofen, diclofenac, indometacin, piroxicam, fenoprofen, flubiprofen, ketoprofen, naproxen, suprofen, loxoprofen, cinnoxicam, tenoxicam, and a combination thereof.

\* \* \* \* \*